US012758242B2

(12) United States Patent
Reindel et al.

(10) Patent No.: US 12,758,242 B2
(45) Date of Patent: Oct. 13, 2026

(54) LAPAROSCOPIC GRASPER WITH FORCE-LIMITING GRASPING MECHANISM

(71) Applicant: Applied Medical Resources Corporation, Rancho Santa Margarita, CA (US)

(72) Inventors: Eric S. Reindel, Encinitas, CA (US); Javid E. Hovaida, Ladera Ranch, CA (US); Kyle R. Fast, Mission Viejo, CA (US); Arkadiusz A. Strokosz, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 68 days.

(21) Appl. No.: 18/769,199

(22) Filed: Jul. 10, 2024

(65) Prior Publication Data

US 2024/0358390 A1 Oct. 31, 2024

Related U.S. Application Data

(63) Continuation of application No. 18/156,314, filed on Jan. 18, 2023, now Pat. No. 12,042,165, which is a continuation of application No. 16/679,664, filed on Nov. 11, 2019, now Pat. No. 11,596,428.

(60) Provisional application No. 62/768,018, filed on Nov. 15, 2018.

(51) Int. Cl.

| | |
|---|---|
| ***A61B 17/00*** | (2006.01) |
| ***A61B 17/29*** | (2006.01) |
| ***A61B 90/00*** | (2016.01) |

(52) U.S. Cl.

CPC .... *A61B 17/29* (2013.01); *A61B 2017/00389* (2013.01); *A61B 2017/00424* (2013.01);

(Continued)

(58) Field of Classification Search

CPC .... A61B 2017/2946; A61B 2019/2947; A61B 17/2909; A61B 17/29; A61B 2017/294; A61B 2017/2939; A61B 2017/2919

See application file for complete search history.

(56) References Cited

U.S. PATENT DOCUMENTS

| | | | |
|---|---|---|---|
| 3,503,396 | A | 3/1970 | Pierie et al. |
| 3,503,397 | A | 3/1970 | Fogarty et al. |

(Continued)

FOREIGN PATENT DOCUMENTS

| | | | |
|---|---|---|---|
| DE | 200 20 192 | U1 | 3/2001 |
| EP | 0 543 107 | A2 | 5/1993 |

(Continued)

OTHER PUBLICATIONS

European Patent Office, Invitation to Pay Additional Fees for International Application No. PCT/US2019/060743, titled “Laparoscopic Grasper with Force-Limiting Grasping Mechanism”, mailed Feb. 5, 2020, 15 pgs.

(Continued)

*Primary Examiner* — Darwin P Erezo
*Assistant Examiner* — Mitchell Brian Hoag
(74) *Attorney, Agent, or Firm* — Jamie Brophy; John Heal

(57) ABSTRACT

A surgical instrument is provided having an actuator mechanism with an integrated extension element. The surgical instrument comprises a handle assembly, an elongate shaft, and an end effector. The end effector can comprise a jaw assembly having atraumatic pads positioned thereon to reduce force on grasped tissue. An actuator is movable within the elongate shaft to actuate jaws of the jaw assembly responsive to movement of a movable handle of the handle assembly. The actuator can have an integrated extension element that allows the actuator to translate within the (Continued)

elongate shaft upon application of a relatively low force and translate and extend upon application of a relatively higher force to the actuator to limit the force applied by the jaw assembly. The actuator is also able to utilize force stored with the integrated extension element to provide a dynamic amount of force used to grasp the tissue in scenarios where the tissue volume decreases while in the jaws.

20 Claims, 13 Drawing Sheets

(52) U.S. Cl.
CPC ............... *A61B 2017/00858* (2013.01); *A61B 2017/00862* (2013.01); *A61B 2017/2901* (2013.01); *A61B 2017/2902* (2013.01); *A61B 2017/2904* (2013.01); *A61B 2017/2905* (2013.01); *A61B 2017/2911* (2013.01); *A61B 2017/2912* (2013.01); *A61B 2017/2913* (2013.01); *A61B 2017/2946* (2013.01); *A61B 2017/2947* (2013.01); *A61B 2017/2948* (2013.01); *A61B 2090/035* (2016.02)

(56) References Cited

U.S. PATENT DOCUMENTS

| | | | | |
|---|---|---|---|---|
| 3,503,398 | A | 3/1970 | Fogarty et al. | |
| 3,515,139 | A | 6/1970 | Mallina | |
| 3,746,002 | A | 7/1973 | Haller | |
| 4,120,302 | A | 10/1978 | Ziegler | |
| 4,821,719 | A | 4/1989 | Fogarty | |
| 5,251,638 | A | 10/1993 | Cottone, Jr. et al. | |
| 5,314,424 | A * | 5/1994 | Nicholas | A61B 17/2909 81/319 |
| 5,395,375 | A | 3/1995 | Turkel et al. | |
| 5,425,743 | A * | 6/1995 | Nicholas | A61B 17/2909 81/331 |
| 5,476,479 | A * | 12/1995 | Green | A61B 17/2909 606/205 |
| 5,489,292 | A | 2/1996 | Tovey et al. | |
| 5,496,333 | A | 3/1996 | Sackier et al. | |
| 5,591,182 | A | 1/1997 | Johnson | |
| 5,626,609 | A * | 5/1997 | Zvenyatsky | A61B 17/29 606/208 |
| 5,643,248 | A | 7/1997 | Yoon | |
| 5,735,874 | A * | 4/1998 | Measamer | A61B 17/2909 81/331 |
| 5,776,146 | A | 7/1998 | Sackier et al. | |
| 5,776,147 | A | 7/1998 | Dolendo | |
| 6,068,624 | A | 5/2000 | Benecke et al. | |
| 6,117,158 | A * | 9/2000 | Measamer | A61B 17/2909 606/208 |
| 6,206,896 | B1 | 3/2001 | Howell et al. | |
| 6,228,104 | B1 | 5/2001 | Fogarty et al. | |
| 6,273,902 | B1 | 8/2001 | Fogarty et al. | |
| 6,387,112 | B1 | 5/2002 | Fogarty et al. | |
| 6,500,189 | B1 | 12/2002 | Lang et al. | |
| 6,530,942 | B2 | 3/2003 | Fogarty et al. | |
| 6,558,408 | B1 | 5/2003 | Fogarty et al. | |
| 6,579,304 | B1 | 6/2003 | Hart et al. | |
| 6,599,295 | B1 * | 7/2003 | Tornier | A61B 17/0401 606/104 |
| 6,626,922 | B1 | 9/2003 | Hart et al. | |
| 6,692,514 | B2 | 2/2004 | Fogarty et al. | |
| 6,719,766 | B1 | 4/2004 | Buelna et al. | |
| 6,874,833 | B2 | 4/2005 | Keith et al. | |
| 6,942,676 | B2 | 9/2005 | Buelna | |
| 6,989,017 | B2 | 1/2006 | Howell et al. | |
| 7,044,946 | B2 | 5/2006 | Nahon et al. | |
| 7,182,775 | B2 | 2/2007 | de Guillebon et al. | |
| 7,291,161 | B2 | 11/2007 | Hooven | |
| 7,347,856 | B2 | 3/2008 | Wittenberger et al. | |
| 7,494,501 | B2 | 2/2009 | Ahlberg et al. | |
| 7,544,200 | B2 | 6/2009 | Houser | |
| 7,819,860 | B2 | 10/2010 | Wittenberger et al. | |
| 7,846,155 | B2 | 12/2010 | Houser et al. | |
| 7,914,524 | B2 | 3/2011 | Wittenberger et al. | |
| 7,918,848 | B2 | 4/2011 | Lau et al. | |
| 7,938,823 | B2 | 5/2011 | Wittenberger et al. | |
| 7,955,325 | B2 | 6/2011 | Wittenberger et al. | |
| 7,981,110 | B2 | 7/2011 | Wittenberger et al. | |
| 8,057,467 | B2 | 11/2011 | Faller et al. | |
| 8,080,004 | B2 * | 12/2011 | Downey | A61B 17/2909 606/1 |
| 8,092,473 | B2 | 1/2012 | Hart et al. | |
| 8,252,021 | B2 | 8/2012 | Boulnois et al. | |
| 8,398,632 | B1 | 3/2013 | Nahon et al. | |
| 8,409,244 | B2 | 4/2013 | Hinman et al. | |
| 8,545,534 | B2 | 10/2013 | Ahlberg et al. | |
| 8,551,077 | B2 | 10/2013 | Main et al. | |
| 8,603,134 | B2 | 12/2013 | Twomey et al. | |
| 8,623,003 | B2 | 1/2014 | Lau et al. | |
| 8,652,165 | B2 | 2/2014 | Haberstich | |
| 8,715,306 | B2 | 5/2014 | Faller et al. | |
| 8,728,118 | B2 | 5/2014 | Hinman et al. | |
| 8,840,639 | B2 | 9/2014 | Gerhardt, Jr. et al. | |
| 8,961,503 | B2 | 2/2015 | Lau et al. | |
| 9,023,079 | B2 | 5/2015 | Boulnois et al. | |
| 9,113,940 | B2 | 8/2015 | Twomey | |
| 9,161,770 | B2 | 10/2015 | Ahlberg et al. | |
| 9,186,165 | B2 | 11/2015 | Twomey et al. | |
| 9,439,647 | B1 | 9/2016 | Bourland, III et al. | |
| 9,610,113 | B2 | 4/2017 | Lau et al. | |
| 9,668,726 | B1 | 6/2017 | Bourland, III et al. | |
| 2003/0028207 | A1 * | 2/2003 | Lang | A61B 17/1611 606/167 |
| 2003/0236537 | A1 | 12/2003 | Hart et al. | |
| 2004/0167552 | A1 | 8/2004 | Buelna et al. | |
| 2005/0192605 | A1 | 9/2005 | Hart et al. | |
| 2005/0240219 | A1 | 10/2005 | Kahle et al. | |
| 2006/0079877 | A1 | 4/2006 | Houser et al. | |
| 2006/0079879 | A1 | 4/2006 | Faller et al. | |
| 2008/0004655 | A1 | 1/2008 | Chiu | |
| 2008/0255608 | A1 * | 10/2008 | Hinman | A61B 17/29 606/205 |
| 2008/0300622 | A1 | 12/2008 | Xu | |
| 2009/0223033 | A1 | 9/2009 | Houser | |
| 2009/0299141 | A1 | 12/2009 | Downey et al. | |
| 2011/0257643 | A1 | 10/2011 | Lau et al. | |
| 2012/0296371 | A1 | 11/2012 | Kappus et al. | |
| 2013/0165927 | A1 | 6/2013 | Nahon et al. | |
| 2014/0243863 | A1 | 8/2014 | Faller et al. | |
| 2014/0358163 | A1 | 12/2014 | Farin et al. | |
| 2015/0148831 | A1 | 5/2015 | Faller et al. | |
| 2015/0335341 | A1 | 11/2015 | Twomey | |
| 2016/0038169 | A1 * | 2/2016 | Twomey | A61B 17/2812 606/206 |
| 2016/0262826 | A1 * | 9/2016 | Allen, IV | A61B 17/295 |
| 2017/0156782 | A1 | 6/2017 | Lau et al. | |
| 2017/0196556 | A1 * | 7/2017 | Shah | A61B 17/1285 |
| 2017/0333030 | A1 | 11/2017 | Bourland, III et al. | |

FOREIGN PATENT DOCUMENTS

| | | | |
|---|---|---|---|
| EP | 0 565 049 | A1 | 10/1993 |
| EP | 0 813 843 | B1 | 12/1997 |
| WO | WO 2007/146842 | A2 | 12/2007 |
| WO | WO 2017/161049 | A1 | 9/2017 |

OTHER PUBLICATIONS

European Patent Office, The International Search Report and Written Opinion forInternational Application No. PCT/US2019/060743, entitled "Laparoscopic Grasper With Force-Limiting Grasping Mechanism," mailed Mar. 26, 2020, 21 pgs.

The International Bureau of WIPO, International Preliminary Report on Patentability for International Application No. PCT/US2019/060743, entitled "Laparoscopic Grasper with Force-Limiting Grasping Mechanism," dated May 27, 2021, 14 pgs.

(56) References Cited

OTHER PUBLICATIONS

European Patent Office, Extended European Search Report for European Patent Application No. 24189265.2, titled "Laparoscopic Grasper with Force-Limiting Grasping Mechanism," dated Oct. 21, 2024, 9 pgs.

* cited by examiner

LAPAROSCOPIC GRASPER WITH FORCE-LIMITING GRASPING MECHANISM

CROSS-REFERENCE TO RELATED APPLICATIONS

This application is a continuation of U.S. patent application Ser. No. 18/156,314 entitled "Laparoscopic Grasper with Force-Limiting Grasping Mechanism" filed on Jan. 18, 2023, which is a continuation of U.S. patent application Ser. No. 16/679,664 entitled "Laparoscopic Grasper with Force-Limiting Grasping Mechanism" filed on Nov. 11, 2019, now U.S. Pat. No. 11,596,428, which claims priority to and benefit of U.S. Provisional Patent Application Ser. No. 62/768,018 entitled "Laparoscopic Grasper with Force-Limiting Grasping Mechanism" filed on Nov. 15, 2018 which is incorporated herein by reference in its entirety.

BACKGROUND

The present application relates to surgical devices and more particularly to instruments for use in minimally-invasive surgery such as laparoscopic grasping instruments.

In general and minimally invasive surgical procedures, surgeons frequently use grasping instruments to grasp and manipulate tissue, vasculature, or other objects within the surgical field. While it is desirable to maintain traction on the grasped tissue, it is undesirable to apply excess force to the tissue. The excess force on the tissue could lead to tissue trauma.

Conventional surgical grasping instruments have included grasping jaws comprised of a metallic material to grasp and manipulate tissue. Certain conventional surgical grasping instruments have also included force limiting mechanisms including relatively complex compression coil spring assemblies that require relatively large shaft diameters to accommodate. Other conventional grasping instruments have included no dedicated force limiting mechanism. Instead, these convention grasping instruments rely on flexibility and compliance of actuating handles to reduce the impact of forceful grasping.

Accordingly, it is desirable to provide a surgical grasping instrument that can reduce the potential for trauma to grasped tissue. It is likewise desirable to provide a surgical grasping instrument that has a simplified mechanism that facilitates relatively low-cost manufacture and assembly. Furthermore, it is desirable to provide a surgical grasping instrument including atraumatic, force limiting features in a device configured for use with a small surgical access port diameter such as a port configured for use with 5 mm instruments.

SUMMARY OF THE INVENTION

In certain embodiments, a surgical grasping instrument is provided herein. The surgical grasping instrument comprises: a handle assembly, an elongate shaft, and a jaw assembly. The handle assembly comprises: a stationary handle, and a movable handle pivotably coupled to the stationary handle. The elongate shaft extends distally from the handle assembly. The elongate shaft has a proximal end coupled to the handle assembly, a distal end opposite the proximal end, and a central longitudinal axis defined by the proximal end and the distal end. The elongate shaft comprises: an outer tube, and an actuator positioned longitudinally within the outer tube. The actuator has a sliding fit within the outer tube and is responsive to pivotal movement of the movable handle. The jaw assembly is disposed at the distal end of the elongate shaft. The jaw assembly comprises a first jaw and a second jaw. The first and second jaws are pivotable between an open configuration of the jaw assembly and a closed configuration of the jaw assembly responsive to pivotal movement of the movable handle. The actuator has a first length along the central longitudinal axis. The actuator comprises an extension element configured to lengthen the actuator to a second length greater than the first length in response to a predetermined force applied to the actuator.

In certain embodiments, a surgical instrument is provided herein. The surgical instrument comprises: a handle assembly; an elongate shaft, and an end effector. The handle assembly comprises: a stationary handle; a movable handle pivotably coupled to the stationary handle; and a locking mechanism. The lock mechanism comprises: a locking member and a lock release. The locking member has a lock portion extending within the handle assembly and a trigger portion extending adjacent an outer surface of the stationary handle. The locking member is movable between a locked position and an unlocked position. The lock release is coupled to the stationary handle. The lock release is configured to maintain the locking member in the locked position. The lock release is actuatable to release the locking member to the unlocked position. The elongate shaft extends distally from the handle assembly. The elongate shaft has a proximal end coupled to the handle assembly, a distal end opposite the proximal end, and a central longitudinal axis defined by the proximal end and the distal end. The elongate shaft comprises an outer tube and an actuator positioned longitudinally within the outer tube. The actuator has a sliding fit with the outer tube and the actuator is responsive to pivotal movement of the movable handle. The actuator has a proximal section extending within the handle assembly to a proximal end. The actuator comprises a locking surface adjacent the proximal end. The lock portion of the locking member is engaged with the locking surface of the actuator with the locking mechanism in the locked position. The end effector is disposed at the distal end of the elongate shaft. The end effector is movable between a first configuration and a second configuration responsive to pivotal movement of the movable handle.

In certain embodiments, a surgical instrument is provided herein. The surgical instrument comprises: a handle assembly; an elongate shaft; and an end effector. The handle assembly comprises: a stationary handle and a movable handle pivotably coupled to the stationary handle. The elongate shaft extends distally from the handle assembly. The elongate shaft has a proximal end coupled to the handle assembly, a distal end opposite the proximal end, and a longitudinal axis defined by the proximal end and the distal end. The elongate shaft comprises: an outer tube, and an actuator positioned longitudinally within the outer tube. The actuator has a sliding fit within the outer tube and is responsive to pivotal movement of the movable handle. The actuator has a length extending along the central longitudinal axis, a height, and a width. The width is substantially smaller than the height such that the actuator has a planar profile. The actuator comprises: a first segment having a first height; and a second segment having a second height smaller than the first height. The second segment defines an extension element longitudinally extendable responsive to force applied to the actuator. The second segment comprises: a plurality of longitudinal sections; a plurality of transverse sections; and a plurality of bends. The plurality of longitudinal sections extends generally parallel to the longitudinal axis. The plurality of transverse sections extends transverse to the longitudinal axis. The plurality of bends are disposed between each longitudinal section of the plurality of longitudinal sections and an adjacent transverse section of the plurality of transverse sections. The end effector is disposed at the distal end of the elongate shaft. The end effector is movable between a first configuration and a second configuration responsive to pivotal movement of the movable handle.

BRIEF DESCRIPTION OF THE DRAWINGS

In order to describe the manner which, the above-recited and other advantages and features of the disclosure can be obtained, a more particular description of the principles briefly described above will be rendered by reference to specific embodiments that are illustrated in the appended drawings. Understanding that these drawings depict only embodiments of the disclosure and are not therefore to be considered to be limiting of its scope, the principles herein are described and explained with additional specificity and detail through the use of the accompanying drawings in which the reference numerals designate like parts throughout the figures thereof.

DETAILED DESCRIPTION OF THE INVENTION

Figure 1:
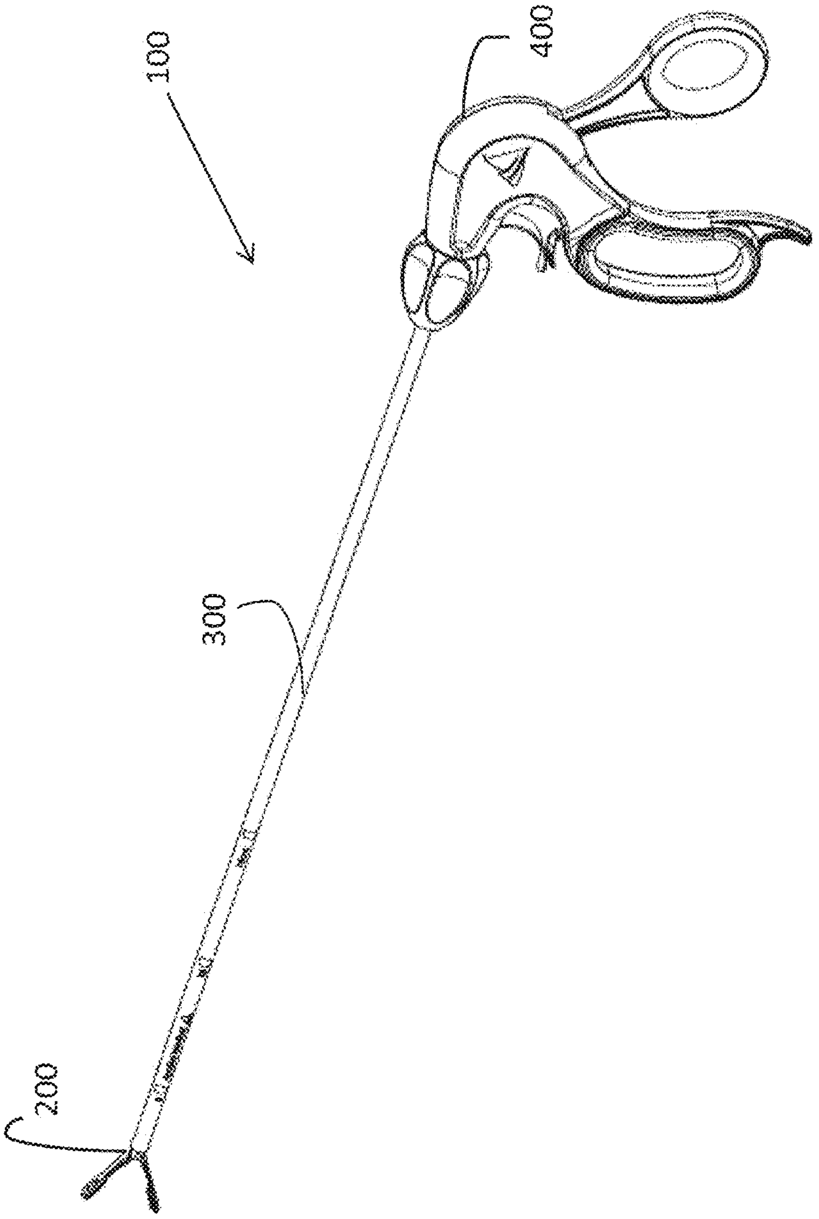
FIG. 1 is a perspective view of an embodiment of a surgical grasping instrument.

With reference to FIG. 1, an embodiment of a surgical grasping instrument 100 is illustrated. The surgical grasping instrument 100 can extend between a proximal end and a distal end and can comprise an end effector such as a jaw assembly 200 at the distal end, a shaft assembly 300 extending between the proximal end and the distal end, and a handle assembly 400 at the proximal end. In some embodiments, the surgical grasping instrument 100 can be configured for use in minimally-invasive surgical procedures such that it is sized and configured to be extended through a trocar cannula or other surgical access port. For example, in some embodiments, the shaft assembly 300 can comprise a generally tubular body having a smooth outer surface and an outer diameter sized for passage through a trocar cannula having a size classification to receive certain instruments such as, for example, a 12 mm trocar, a 10 mm trocar, and a 5 mm trocar. In other embodiments, certain aspects of the surgical instruments described herein can be adapted for use with surgical access ports having different sizes or in open surgical procedures.

Figure 2:
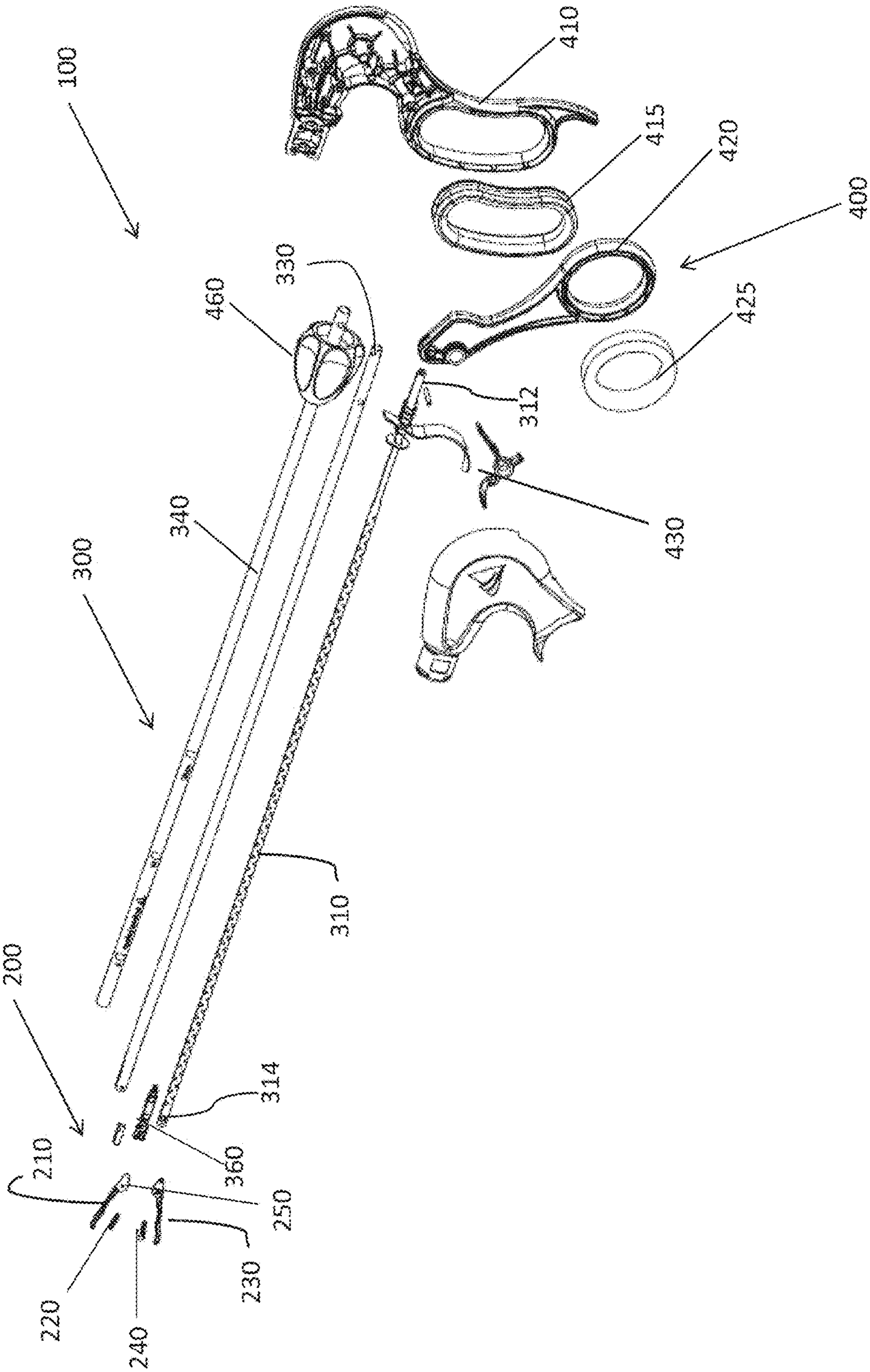
FIG. 2 is an exploded view of the grasping instrument of FIG. 1.
Figure 2A:
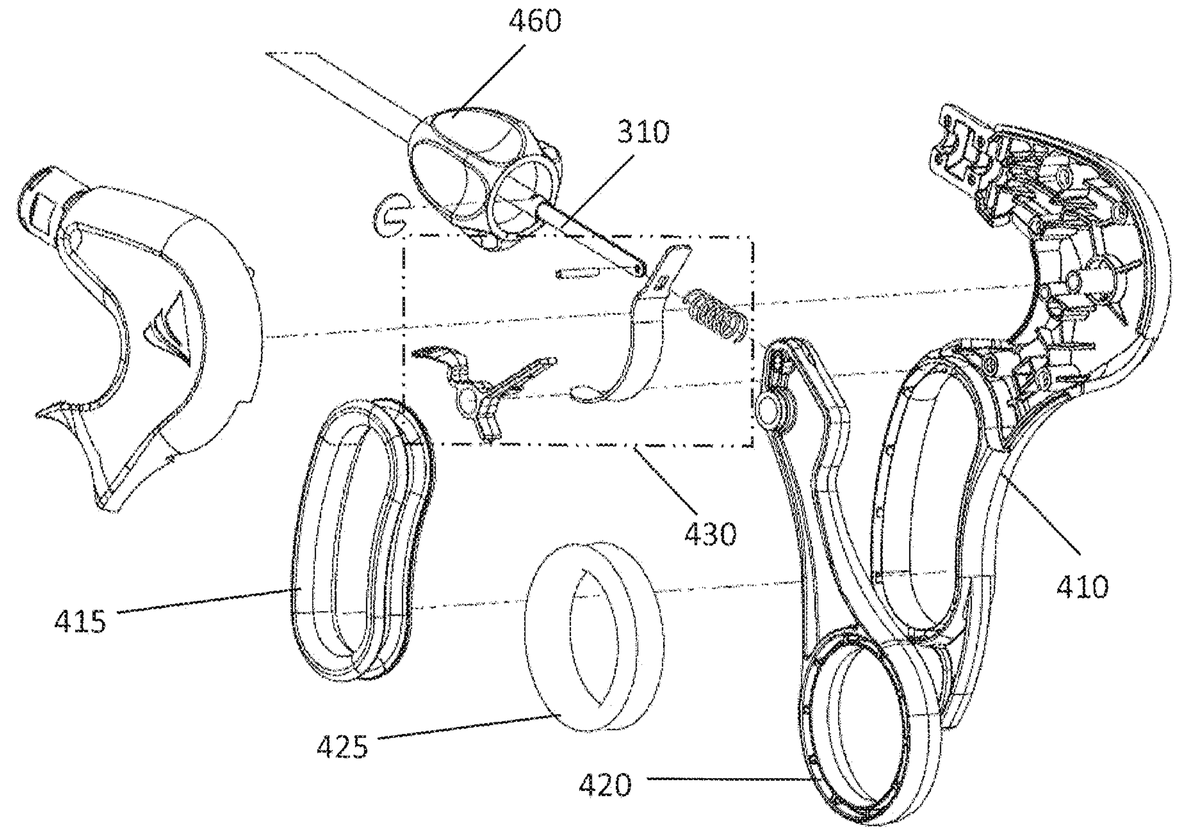
FIG. 2A is an exploded view of the handle assembly of the grasping instrument of FIG. 1.
Figure 2B:
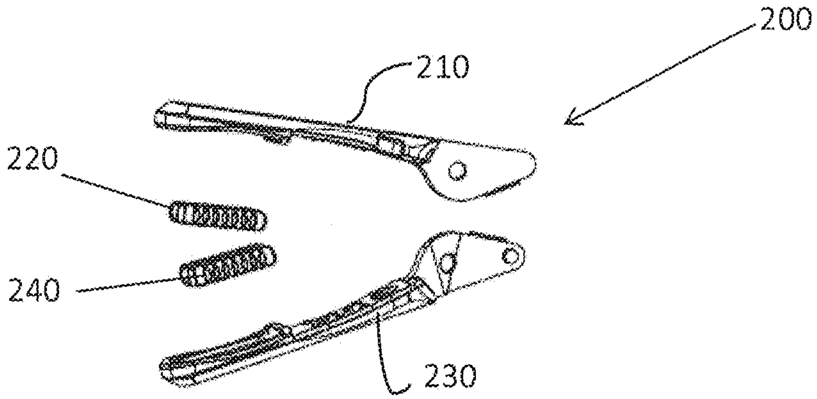
FIG. 2B is an exploded view of the jaw assembly of the grasping instrument of FIG. 1.

With reference to FIG. 2 and FIG. 2B, an exploded view of the surgical grasping instrument 100 of FIG. 1 is illustrated. In the illustrated embodiment, the jaw assembly 200 of the surgical grasping instrument 100 comprises a first jaw 210 coupled to a second jaw 230 at a pivot 250. Thus, by pivoting the first and second jaws 210, 230 with respect to one another, the jaw assembly 200 can be actuated between an open configuration in which the first jaw 210 is spaced from the second jaw 230 and a closed configuration in which the first jaw 210 is approximated with the second jaw 230 to grasp an object such as tissue, vasculature, or another surgical instrument therebetween.

In some embodiments, the jaw assembly 200 can be configured to reduce the potential for tissue trauma during use. For example, the first and/or second jaws 210, 230 can include an atraumatic pad formed thereon. As illustrated in both FIG. 2 and FIG. 2B, the first jaw 210 comprises a first atraumatic jaw pad 220 and the second jaw 230 comprises a second atraumatic jaw pad 240. In some embodiments, the first and second atraumatic pads 220, 240 can comprise soft, relatively low durometer atraumatic pads sold under the trademark LATIS®. In other embodiments, the jaw assembly 200 can include pad-less first and second jaws 210, 230 and pressure reduction at the jaws can be enhanced by a force reducing or limiting actuation mechanism.

Figure 2C:
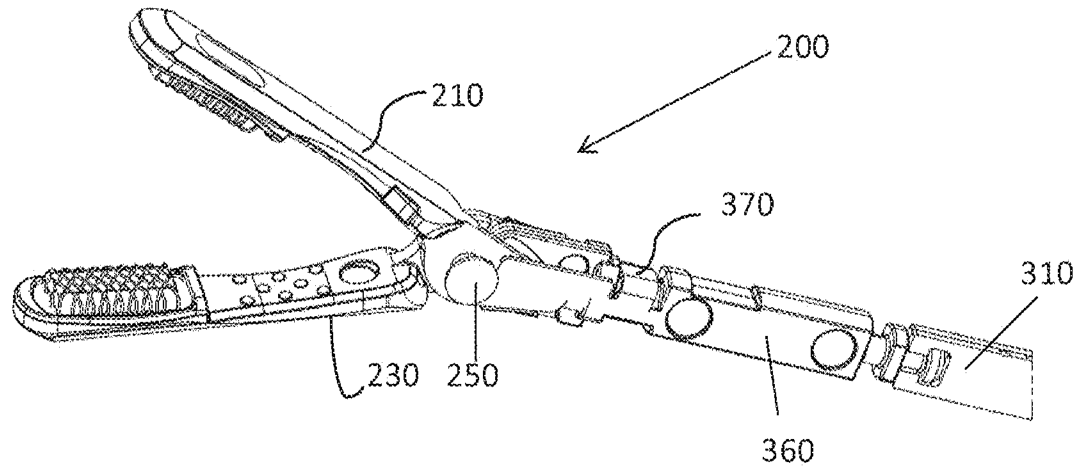
FIG. 2C is an exploded view of the jaw assembly coupled to a distal end of an actuator having a tracked head member of the grasping instrument of FIG. 1.
Figure 2D:
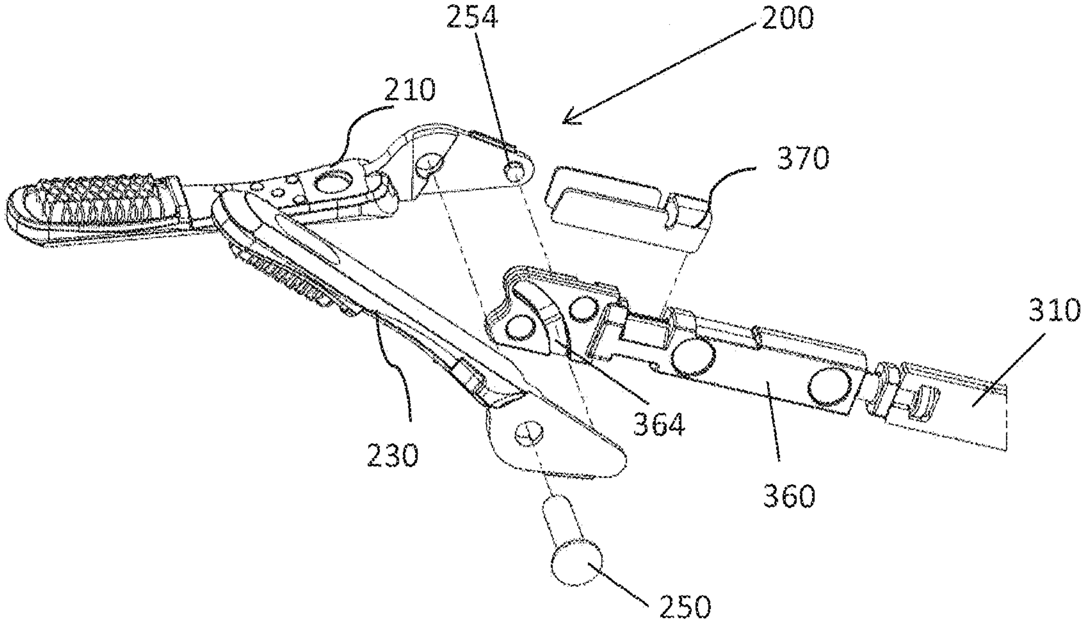
FIG. 2D is an exploded view of the jaw assembly, tracked head member, and actuator of FIG. 2C.

With reference to FIG. 2, FIG. 2C, and FIG. 2D, an exploded view of the surgical grasping instrument 100 of FIG. 1 is illustrated. In the illustrated embodiment, the first and second jaws 210, 230 are pivotally coupled to one another and to shaft (not illustrated) at the pivot 250. An actuation post or pin 254 protrudes from each of the first and second jaws 210, 230 proximal of engagement with the pivot 250. The jaw assembly 200 is coupled to the distal end of the actuator 310 by a head member 360, which is positioned between proximal ends of each of the first and second jaws 210, 230. Each side of the head member 360 has a track 364 formed therein. The actuation posts or pins 254 of each of the first and second jaws 210, 230 are positioned within respective tracks 364 such that proximal and distal movements of the actuator 310 and head member 360 with respect to the outer tube of the shaft moves the actuation pins 254 to open and close the first and second jaws 210, 230. A shim 370 can be positioned at the distal end of the head member 360 to maintain a desired spacing of the jaw assembly 200 and head member 360 within the outer tube. In the illustrated embodiment, the shim 370 can have a saddle configuration positioned astride the head member 360 and proximal ends of the first and second jaws 210, 230 to reduce any tendency of the actuation post or pin 254 to become disengaged from the track 364 under load.

With continued reference to FIG. 2, the elongate shaft assembly 300 can comprise an actuator 310, an outer tube 330 and a dielectric sleeve 340. The actuator can be slidably positioned within the outer tube 330. The dielectric sleeve 340 can be disposed around an outer surface of the outer tube 330 and provide electrical insulation for the elongate shaft assembly 300. In certain embodiments, the actuator 310 can comprise a substantially planar member extending generally longitudinally between a proximal end 312 and a distal end 314. The substantially planar geometry of the actuator 310 can be defined by a length between the proximal end 312 and the distal end 314, a height orthogonal to the length, and a width orthogonal to both the length and the height. The width is substantially smaller than the height and the length. In certain embodiments, the actuator 310 can comprise a stack of a plurality of actuator strips, such as, for example, two actuator strips to provide an actuator 310 having desired stiffness, extension, and fatigue life characteristics.

With continued reference to FIG. 2 and FIG. 2A, in the illustrated embodiment, the handle assembly 400 comprises a housing formed of a pair of housing halves that define a stationary handle 410, a movable handle 420 pivotably coupled to the stationary handle 410 at a pivot pin of a locking mechanism 430, and a rotation knob 460. In the illustrated embodiment, the stationary handle 410 can be contoured to be grasped in the fingers of a user's hand and the movable handle 420 can include a thumb ring to be engaged by a user's thumb and moved by flexion and extension of the user's thumb. It is contemplated that in other embodiments, other configurations of handle assembly can be used with the elongate shaft assemblies and end effector assemblies described herein.

Figure 3:
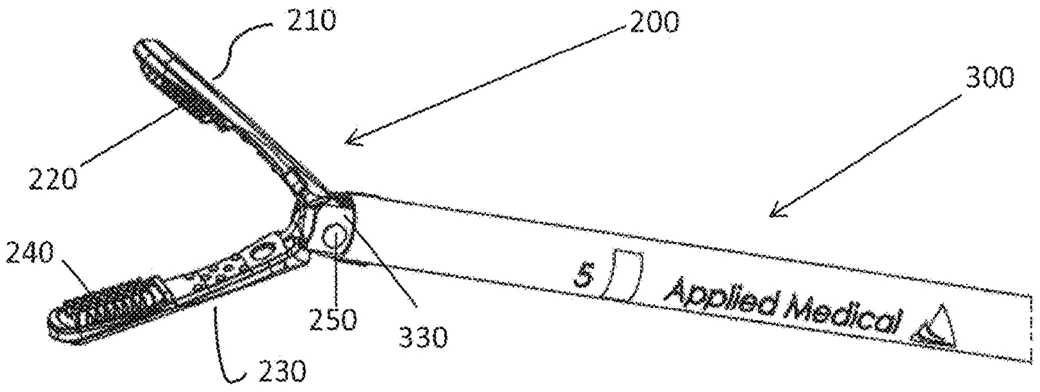
FIG. 3 is a side view of a jaw assembly of the grasping instrument of FIG. 1 with the jaw assembly in an open configuration.
Figure 4:
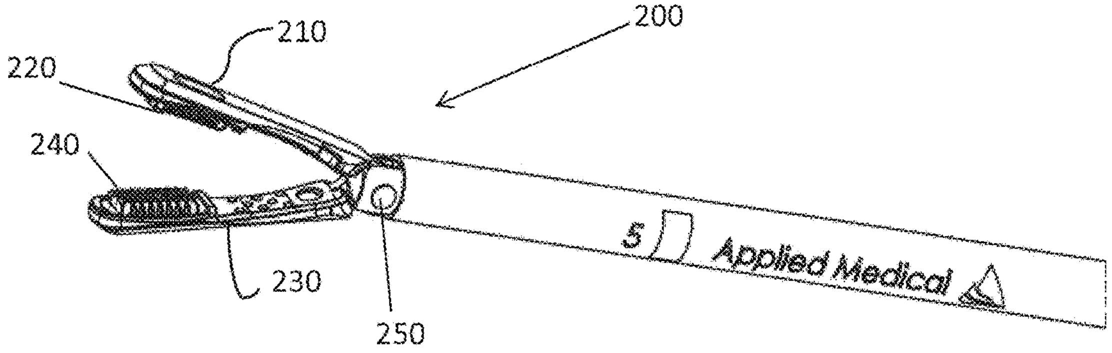
FIG. 4 is a side view of a jaw assembly of the grasping instrument of FIG. 1 with the jaw assembly in a partially closed configuration.
Figure 5:
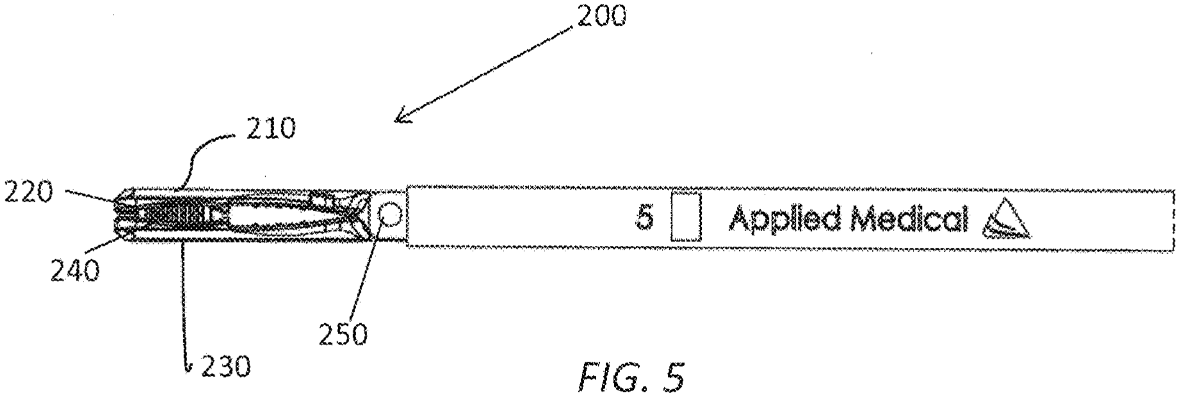
FIG. 5 is a side view of a jaw assembly of the grasping instrument of FIG. 1 with the jaw assembly in a closed configuration.
Figure 3A:
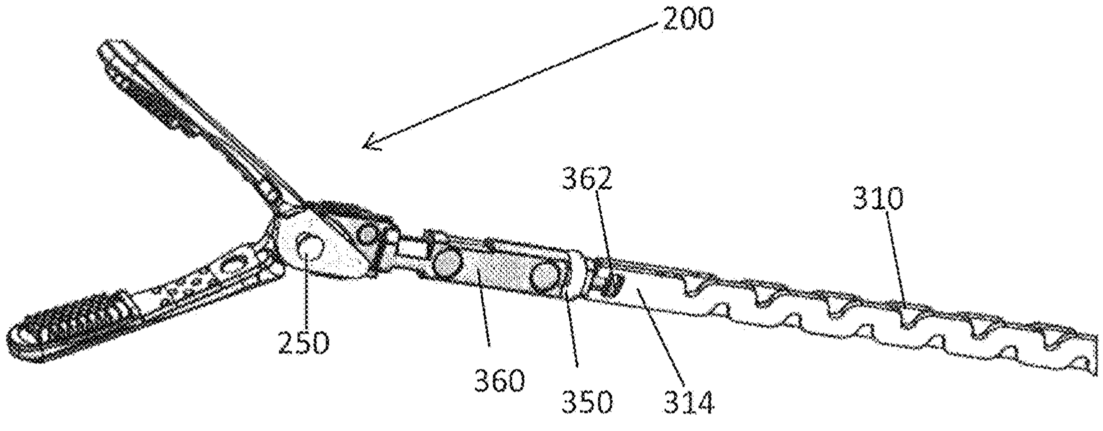
FIG. 3A is a side view of a jaw assembly of the grasping instrument of FIG. 1 with the jaw assembly in an open configuration and with an outer tube and sleeve removed.
Figure 4A:
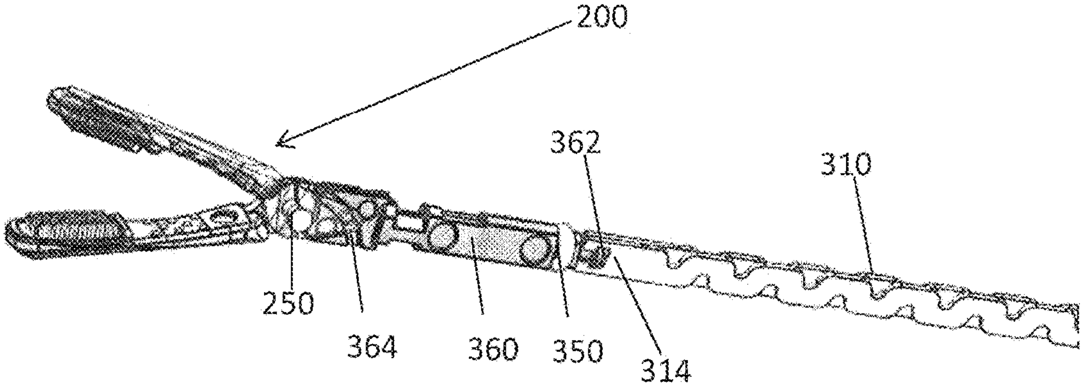
FIG. 4A is a side view of a jaw assembly of the grasping instrument of FIG. 1 with the jaw assembly in a partially closed configuration and with an outer tube and sleeve removed.
Figure 5A:
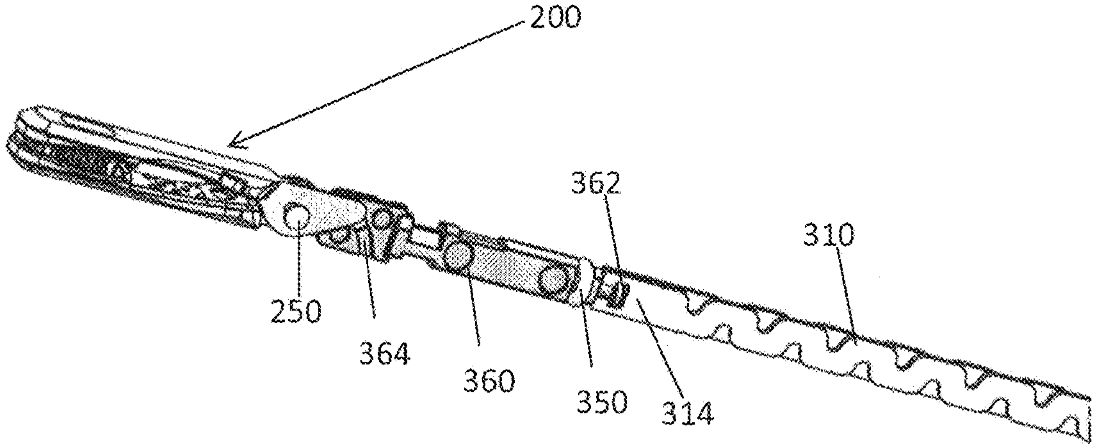
FIG. 5A is a side view of a jaw assembly of the grasping instrument of FIG. 1 with the jaw assembly in a closed configuration and with an outer tube and sleeve removed.

With reference to FIG. 3-FIG. 5 and FIG. 3A-FIG. 5A, the jaw assembly 200 of the surgical grasping instrument is illustrated in open (FIG. 3 and FIG. 3A), partially closed (FIG. 4 and FIG. 4A), and closed configurations (FIG. 5 and FIG. 5A). As illustrated in FIGS. 3 and 3A, with the jaw assembly 200 in the open configuration, the first jaw 210 is spaced from the second jaw 230 such that a user can position the surgical grasping instrument in a surgical site with an object to be grasped positioned between the first and second jaws 210, 230. The first jaw 210 and the second jaw 230 are pivotably coupled to one another at a pivot 250 such as a linkage rivet, pin, or other pivotable assembly.

With continued reference to FIG. 3 and FIG. 3A, the pivot 250 is also coupled to the outer tube 330 of the elongate shaft assembly 300 at the distal end of the elongate shaft assembly 300. The elongate shaft assembly 300 can further comprise a head member 360 that engages the first and second jaws 210, 230 of the jaw assembly 200 at engagement locations proximal the pivot 250. For example, in certain embodiments, the first and second jaws 210, 230 can each comprise an actuation pin protruding radially inwardly with respect to the elongate shaft assembly 300 at a location proximal the pivot 250, and the head member 360 can include a first groove, slot, or track 364 positioned to receive the actuation pin of the first jaw 210 and a second groove, slot, or track formed therein positioned to receive the actuation pin of the second jaw 230. The first track and the second track can extend transversely relative to the central longitudinal axis of the elongate shaft assembly 300 such that proximal and distal movement of the head member 360 pivots the first and second jaws 210, 230 relative to one another about the pivot 250.

With continued reference to FIG. 3 and FIG. 3A, in some embodiments, the elongate shaft assembly 300 can further include a jaw support member such as at least one shim member positioned within the outer tube 330 at the distal end to longitudinally align and maintain spacing of the head member 360 and the jaw assembly 200 relative to the central longitudinal axis. In the illustrated embodiments, the elongate shaft assembly 300 can include a seal element 350 disposed between the head member 360 and an inner surface of the outer tube 330 to prevent fluid and gas ingress or leakage from a surgical site into the elongate shaft assembly. For example, the elongate shaft assembly 300 can comprise an O-ring disposed retained by a groove in the head member 360.

With continued reference to FIG. 3 and FIG. 3A, a proximal end of the head member 360 can be coupled to a distal end of the actuator 310. In some embodiments, the proximal end of the head member 360 and the distal end of the actuator 310 can be configured to provide a coupling that is rotatable about the central longitudinal axis of the elongate shaft assembly 300. For example, as illustrated, the proximal end of the head member 360 comprises a protruding annular post 362, and the distal end 314 of the actuator 310 can comprise a cutout sized and configured to receive the annular post 362 and allow rotation of the jaw assembly 200 relative to the central longitudinal axis of the elongate shaft assembly 300. As further described with reference to FIG. 6, rotation of the rotation knob 460 of the handle assembly 400 can thus rotate the outer tube 330 of the elongate shaft assembly 300 to rotate the jaw assembly 200 to a desired orientation relative to the central longitudinal axis.

With continued reference to FIG. 3 and FIG. 3A, in some embodiments, the head member 360 can be formed by a metal injection molding (MIM) process. Advantageously, this MIM process can allow the efficient, rapid manufacture of a head member 360 of a metallic material having desirable strength and fatigue life characteristics and being formed to have desired geometric features, with integrated tracks or slots to engage the jaw assembly 200 and a post or positioning pin to engage the actuator 310 as described above. In other embodiments, the head member 360 can be formed of a metallic material that has been cast, machined, or otherwise processed to have the desired geometry. In other embodiments, the head member 360 can be formed of a non-metallic material.

With reference to FIG. 4 and FIG. 4A, an embodiment of jaw assembly 200 is illustrated in a partially closed configuration. As illustrated, proximal translation of the actuator 310 along the central longitudinal axis pivots the first jaw 210 and the second jaw 230 relative to one another to approximate the first jaw pad 220 and the second jaw pad 240.

With continued reference to FIG. 4 and FIG. 4A, the first jaw 210 and the second jaw 230 have the same geometric features and pivot about the same pivot axis, which extends transversely to the central longitudinal axis. In the illustrated embodiment, the pivot axis of the first and second jaws 210, 230 extend generally perpendicularly to the central longitudinal axis. The first jaw 210 has a generally elongate configuration defining a first jaw axis, and the second jaw 230 has a generally elongate configuration defining a second jaw axis. In certain embodiments, proximal translation of the actuator 310 pivots the first and second jaws 210, 230 from an open position in which an angle defined between the first jaw axis and the second jaw axis is approximately 45 degrees, and a closed position in which the angle defined between the first jaw axis and the second jaw axis is approximately 0 degrees.

With reference to FIGS. 5 and 5A, an embodiment of jaw assembly 200 is illustrated in a closed configuration. In the closed configuration, the first jaw 210 and the second jaw 230 are approximated such that the first jaw pad 220 is adjacent the second jaw pad 240 or separated by an object being grasped. As noted above, the first jaw pad 220 and second jaw pad 240 can be formed of a material selected to be atraumatic to tissue grasped therebetween. Moreover, the first jaw pad 220 and second jaw pad 240 can be disposed over a relatively large surface area relative to the first jaw 210 and the second jaw 230. For example, desirably, the first and second jaw pads 220, 240 can extend along at least about 20% of a length of the first and second jaws 210, 230 distal the pivot 250. More desirably, the jaw pads 220, 240 can extend along at least about 25% of a length of the first and second jaws 210, 230 distal the pivot 250. Advantageously, this relatively large atraumatic contact surface can distribute pressure applied to a grasped object over a large surface area to reduce the risk of trauma to grasped tissue. Moreover, the first and second jaw pads 220, 240 can be disposed at a transverse angle relative to a longitudinal axis defined by respective first and second jaws 210, 230. Thus, the angular seating of the first and second jaw pads 220, 240 can tend to draw a grasped object proximally with respect to the central longitudinal axis. This angular seating of the first and second jaw pads 220, 240 can advantageously increase the tractive ability of the surgical grasping instrument without significantly increasing the pressure applied to a grasped object.

With continued reference to FIG. 5, in the illustrated embodiment of the jaw assembly 200, the first and second jaws 210, 230 can be configured to further reduce the incidence of trauma to tissue in the surgical site, the surgical access port, and other surgical instruments. For example, the first and second jaws 210, 230 can each be formed of a composite construction comprising a rigid metallic inner jaw spine to which an atraumatic non-metallic outer surface is applied. The first and second jaw pads 220, 240 can be disposed on the atraumatic non-metallic outer surface. Desirably, in some embodiments, the first and second jaws 210, 230 can each comprise a metallic inner jaw spine to which a plastic overmolded outer surface is applied. The plastic overmolds can each have a pad surface sized and be configured to receive the respective first and second jaw pads 220, 240. The pad surfaces can be formed at a transverse angle relative to a longitudinal axis of the respective first and second jaws 210, 230 to position the first and second jaw pads 220, 240 at an angled orientation. The first and second jaw pads 220, 240 can be adhered or otherwise bonded to the pad surface.

Figure 6:
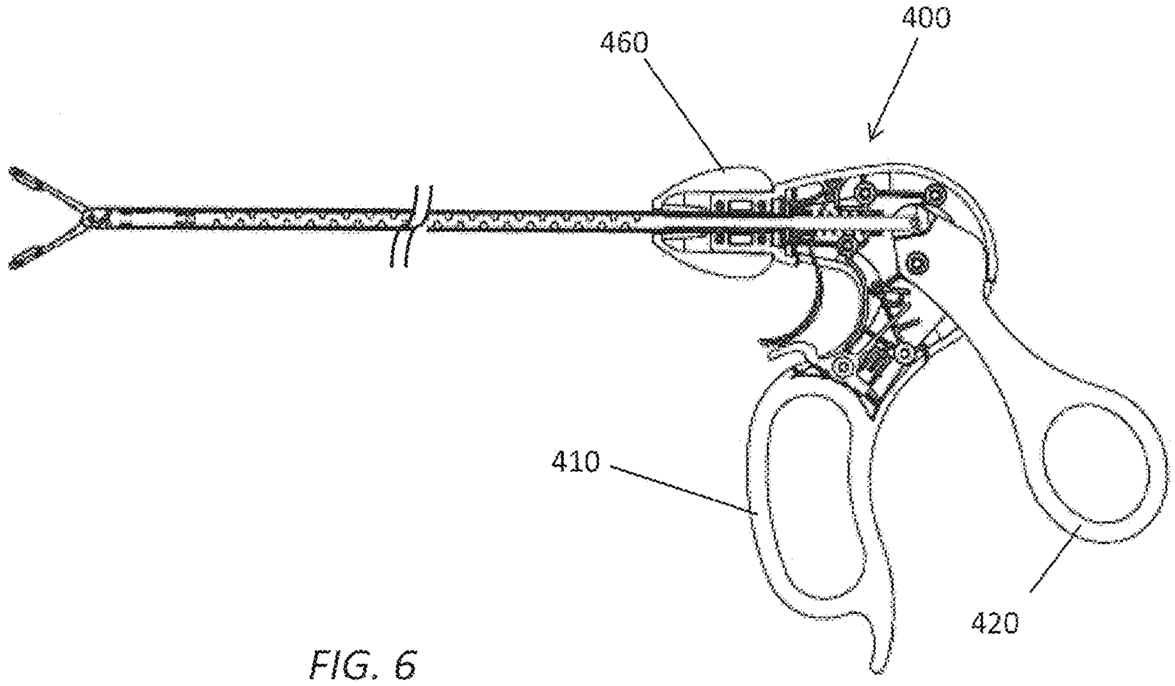
FIG. 6 is a partial cut away side view of a handle assembly of the grasping instrument of FIG. 1 positioned with the jaw assembly in an open configuration.

With reference to FIG. 6, an embodiment of the handle assembly 400 for the surgical grasping instruments 100 described herein is illustrated. As illustrated, the movable handle 420 is spaced from the stationary handle 410 to position the jaw assembly 200 in an open configuration, as illustrated in FIG. 3. Desirably, in certain embodiments, the stationary handle 410 can have an ergonomic finger grip comprising an elastomeric finger grip insert 415 (FIG. 2) removably positioned in the grip to provide a soft touch surface for a user. Likewise, a thumb ring of the movable handle 420 can comprise an elastomeric thumb ring insert 425 (FIG. 2) removably positioned in the thumb ring to provide a soft touch surface for a user. A user can additionally rotate rotation knob 460 relative to the handle assembly 400 to rotate the outer tube 330 relative to the handle assembly 400. For example, the handle assembly 400 can be configured with an ergonomic profile such that a user's index finger can easily be extended to rotate the rotation knob 460. This rotation can orient the jaw assembly 200 coupled to the outer tube 330 in a desired orientation about tissue, vasculature, or another object to be grasped.

Figure 7:
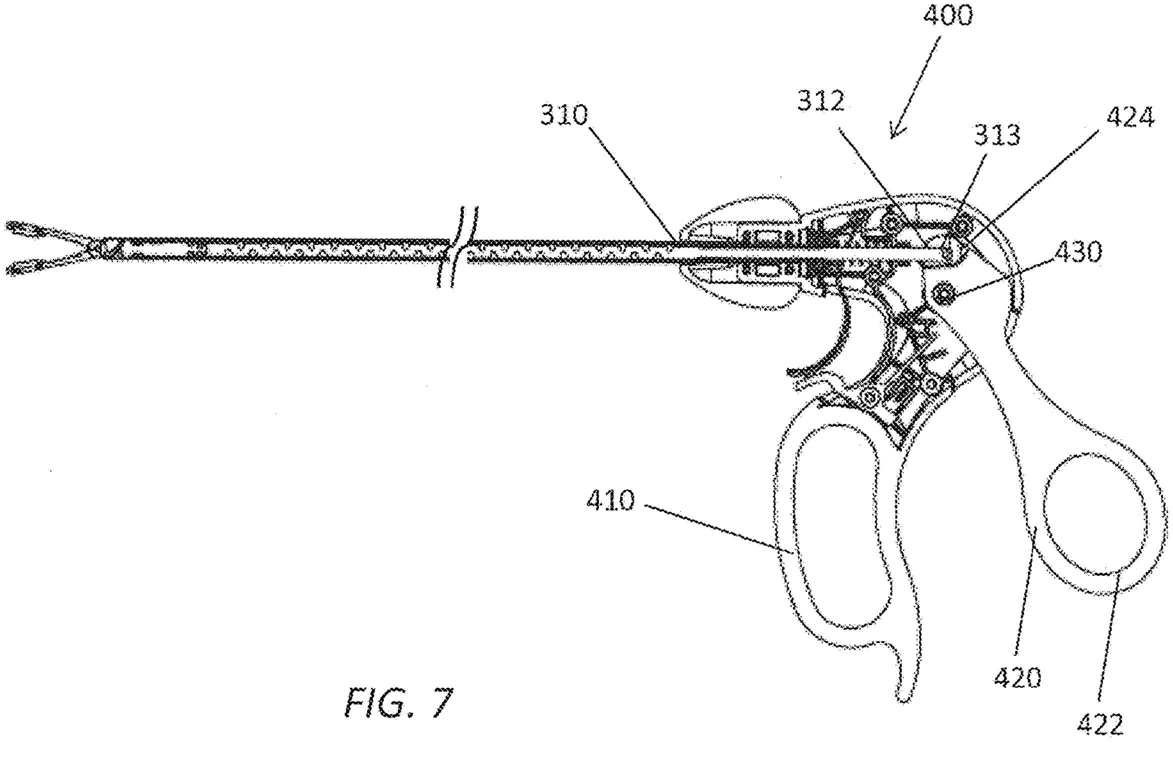
FIG. 7 is a partial cut away side view of a handle assembly of the grasping instrument of FIG. 1 positioned with the jaw assembly in a partially closed configuration.

With reference to FIG. 7, the handle assembly 400 is illustrated in a partially closed configuration corresponding to the jaw assembly 200 in a partially closed configuration as illustrated in FIG. 4. In the partially closed configuration, the movable handle 420 is pivoted relative to the stationary handle 410 about the pivot pin of the locking mechanism 430. In the illustrated embodiment, the movable handle extends from a first end 422 having the thumb ring to a second end 424. The pivot pin of the locking mechanism 430 is disposed between the first end 422 and the second end 424. The second end 424 of the movable handle 420 is coupled to the proximal end 312 of the actuator 310. In some embodiments the proximal end 312 of the actuator 310 can comprise a proximal coupler 313 such as a recess, bore, slot, or other feature that is configured to be coupled to with the second end 424 of the movable handle 420 and allow the transfer of force therebetween. In the illustrated embodiment, the proximal coupler comprises a bore that can receive a post protruding from the second end 424 of the movable handle 420 or can be coupled thereto by a coupling pin or rivet. Thus, as the movable handle 420 is pivoted about the pivot pin of the locking mechanism 430, the actuator 310 is pulled proximally with respect to the central longitudinal axis. This proximal movement likewise moves the head member 360 of the elongate shaft assembly 300 proximally to close the jaw assembly 200, as shown in FIG. 4.

Figure 8:
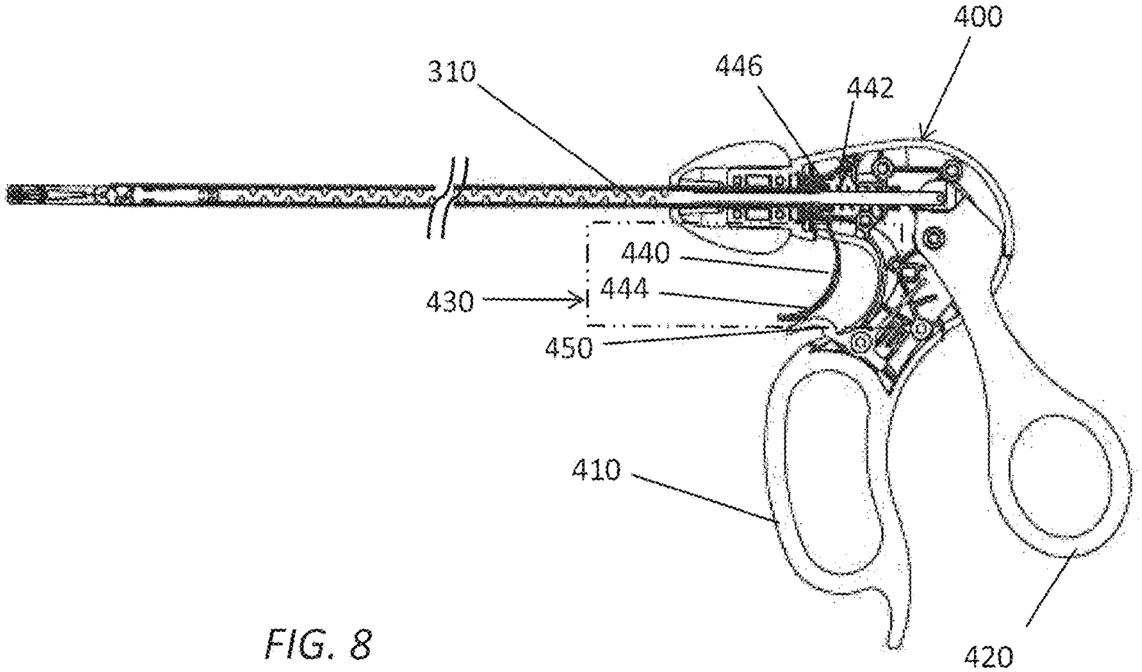
FIG. 8 is a partial cut away side view of a handle assembly of the grasping instrument of FIG. 1 positioned with the jaw assembly in a closed configuration with a latch mechanism engaged in a latched configuration.
Figure 9:
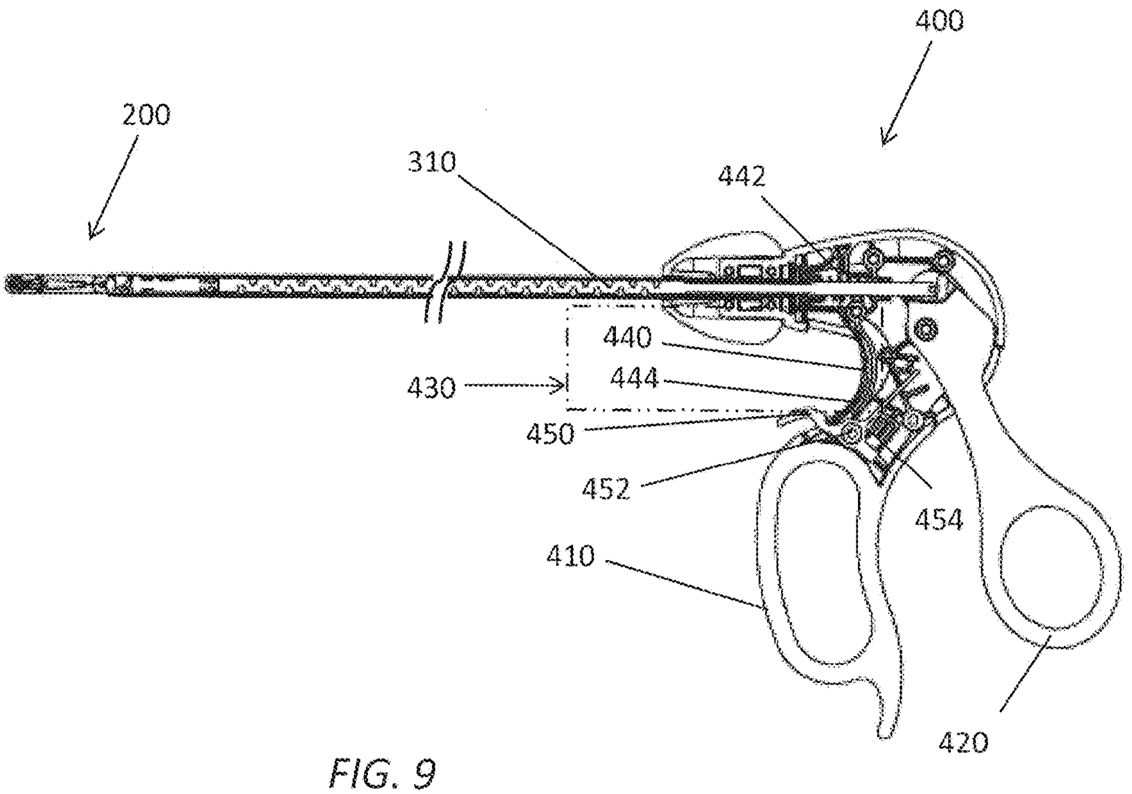
FIG. 9 is a partial cut away side view of a handle assembly of the grasping instrument of FIG. 1 positioned with the jaw assembly in a closed configuration with a latch mechanism engaged in an unlatched configuration.

With reference to FIG. 8 and FIG. 9, further movement of the movable handle 420 can further actuate the surgical grasping instrument to move the jaw assembly 200 to a closed configuration as shown in FIG. 5. In some embodiments, the handle assembly 400 further comprises the locking mechanism therein to maintain the movable handle 420 in a desired position relative to the stationary handle 410. In certain embodiments, the locking mechanism 430 can comprise a trigger lock 440 and a lock release 450 that are actuated by a user to latch and unlatch the locking mechanism.

With continued reference to FIG. 8 and FIG. 9, an embodiment of the locking mechanism 430 is illustrated in latched (FIG. 8) and unlatched (FIG. 9) configurations. The trigger lock 440 of the locking mechanism 430 extends from a first end having a trigger portion 444 extending adjacent the stationary handle 410 to a second end having a locking portion 442 and positioned within the handle assembly 400 adjacent the actuator 310. In some embodiments, the actuator 310 can have an engagement surface such as a latch recess formed therein and sized and configured to be selectively engaged by the locking portion 442 of the trigger lock 440 when the locking mechanism 430 is in a latched configuration. The locking mechanism 430 can further comprise a locking spring 446 within the handle assembly to bias the locking portion 442 of the trigger lock 440 to maintain the engagement of the locking portion 442 with the latch recess when the locking mechanism 430 is in the latched configuration.

With reference to FIG. 8, with the locking mechanism 430 in a latched configuration, the locking portion 442 of the trigger lock 440 is positioned and oriented to restrict the actuator 310 from freely translating proximally and distally with respect to the central longitudinal axis. For example, in some embodiments, the locking portion 442 can comprise a passage or generally rectangular window formed therein through which the actuator 310 can freely translate when the locking portion 442 is oriented generally perpendicularly to the actuator 310 (as illustrated in FIG. 9) and which engages the actuator 310 when passage of the locking portion is misaligned with an axis perpendicular to the longitudinal axis of the actuator (FIG. 8). The locking spring 446 biases the locking portion 442 of the trigger lock 440 into binding engagement with the actuator 310 once the lock release 450 has been depressed to allow the trigger lock 440 to separate from the stationary handle 410. Thus, this engagement between the trigger lock 440 and actuator 310 locks the jaw assembly 200 in a desired position.

In some embodiments, the trigger lock 440 of the locking mechanism 430 may define a reverse limit for the jaw assembly 220 preventing attempts by the jaw assembly 220 to revert from the closed position to the open position beyond the point defined by the locking mechanism 430. However, the restrictions imposed by the trigger lock 440 may not define a forward limit corresponding to an extent the jaw assembly 220 compresses the tissue in the closed position.

With reference to FIG. 9, when a user desires to reposition the first and second jaws to grasp tissue specimens, the movable handle 420 can be moved to a desired position such as a partially closed or closed position with the locking mechanism 430 in an unlatched configuration having the trigger lock 440 approximated with the stationary handle 410 by latching engagement with the lock release 450. As illustrated, an end of the trigger portion 444 can be advanced over the lock release 450 and maintained adjacent the stationary handle 410 by the lock release 450. With the trigger lock 440 positioned adjacent the stationary handle 410, the locking portion 442 of the trigger lock 440 is oriented to allow free translation of actuator 310 through the passage formed in the locking portion 442 responsive to movement of the movable handle 420.

With continued reference to FIG. 9, in certain embodiments, the lock release 450 can be pivotally coupled to the stationary handle 410 at a lock release pivot 452. The lock release 450 can be biased to maintain the trigger portion 444 of the trigger lock 440 adjacent the stationary handle 410. In the illustrated embodiment, the lock release 450 can be biased with a lock release spring 454 disposed within the handle assembly. In is contemplated that in other embodiments, the lock release 450 can be formed of a flexible member extending from the stationary handle 410 with the desired bias and without a lock release pivot. When a user desires to engage the locking mechanism 430 to maintain a fixed position of the movable handle 420, actuator 310, and jaw assembly 200, the user can depress the lock release 450 to overcome the bias of the lock release spring 454 and pivot the lock release 450 out of engagement with the end of the trigger portion 444 of the trigger lock 440.

Figure 10:
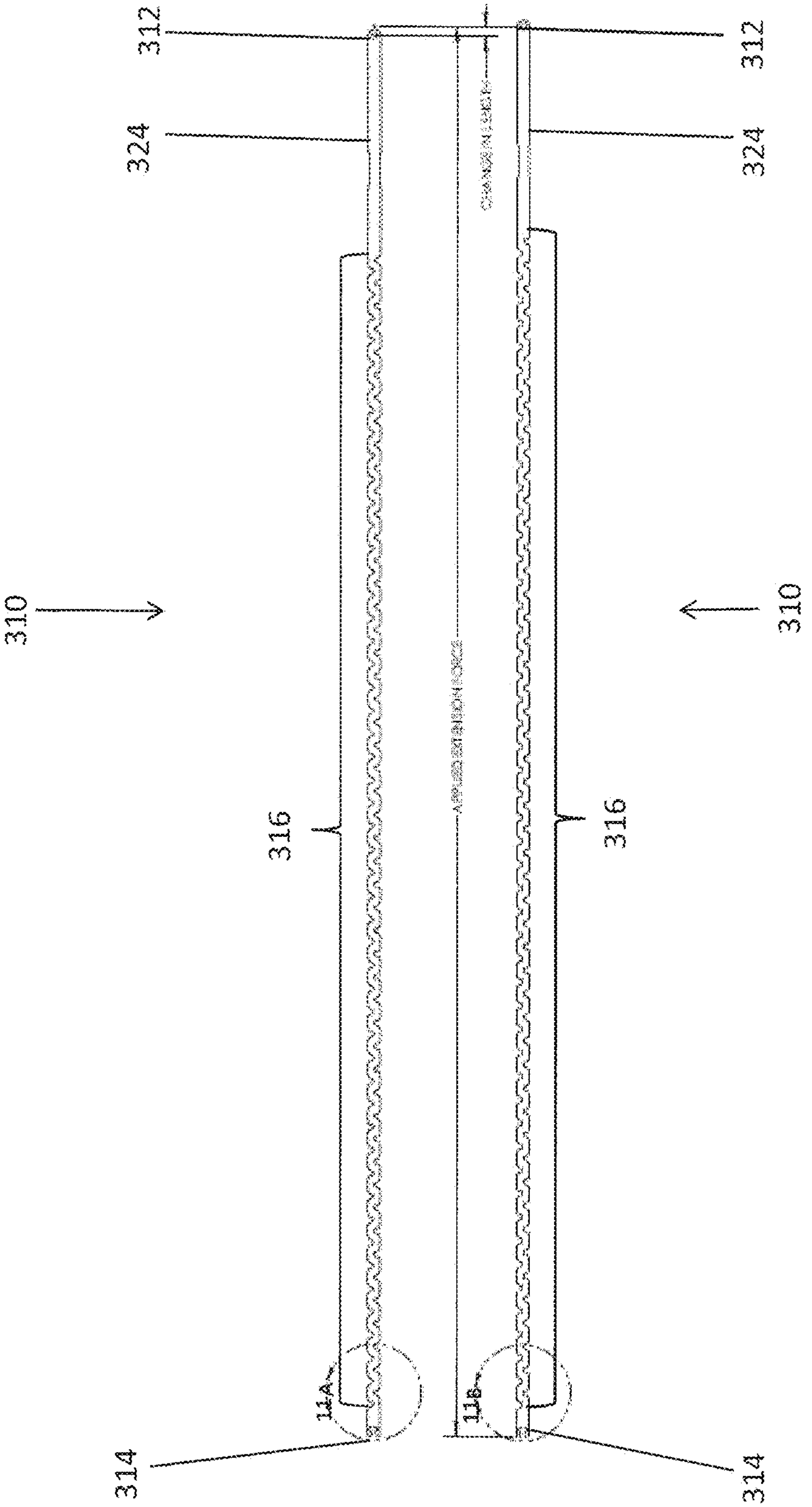
FIG. 10 is a side view of an actuator of shaft assembly of the grasping instrument of FIG. 1 in an undisturbed state and an extended state.

With reference to FIG. 10, an embodiment of actuator 310 for use in the elongate shaft assemblies described herein is illustrated in undisturbed (upper) and extended (lower) states. The actuator 310 has a substantially planar configuration with a significantly small width relative to its length and height. Advantageously, this planar configuration can be efficiently manufactured from a coil or sheet of a metallic material that can be heat treated to achieve desired tensile strength and durability characteristics. For example, in some embodiments, the actuator 310 can be stamped from a sheet of a metallic material having desired structural properties. In some embodiments, the actuator 310 can be formed from a metallic material such as a coil sheet of 17-7 PH stainless steel. In certain embodiments of the surgical grasping instrument, two or more stamped sheet actuators can be arranged in parallel in an adjoining orientation to achieve desired extension properties and durability characteristics while being relatively rapidly manufacturable by progressive stamping. In some embodiments, the actuator 310 can be configured to limit the force applied to an object being grasped, which advantageously can reduce the incidence of trauma to grasped tissue.

With continued reference to FIG. 10, in some embodiments, the actuator 310 can comprise a segment formed to define an integrated extension element 316. Advantageously, the extension element 316 can function as a force-limiting spring mechanism for the actuator 310 having an integrated construction that allows for low-cost, efficient manufacture of the actuator 310. As illustrated, the extension element 316 can be disposed between the proximal end 312 and distal end 314 of the actuator 310, with the remaining segments of the actuator defining a non-extending, or rigid elements 324. As illustrated, in one embodiment, the extension element 316 can have a height orthogonal to the length of the actuator 310 that is smaller than a corresponding height of the rigid elements 324. In the illustrated embodiment, the extension element 316 comprises a height that is approximately half of the height of the rigid elements 324.

Figure 11A:
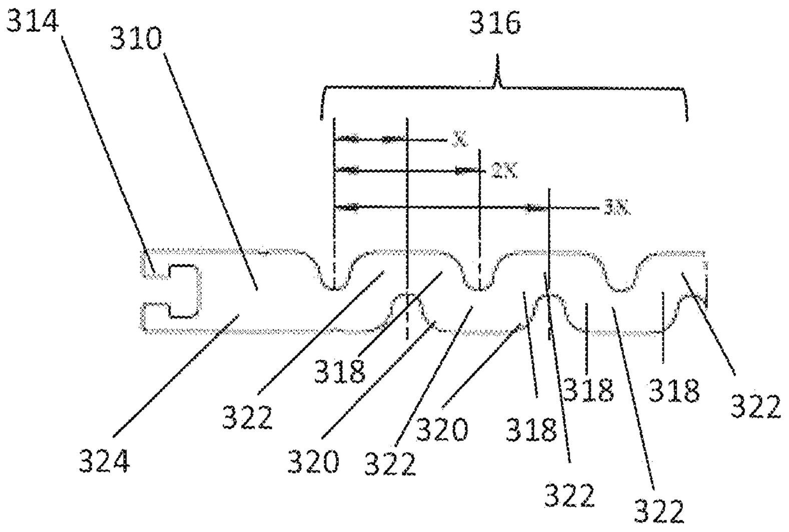
FIG. 11A is a side view of a portion of the actuator of FIG. 10 in the undisturbed state.
Figure 11B:
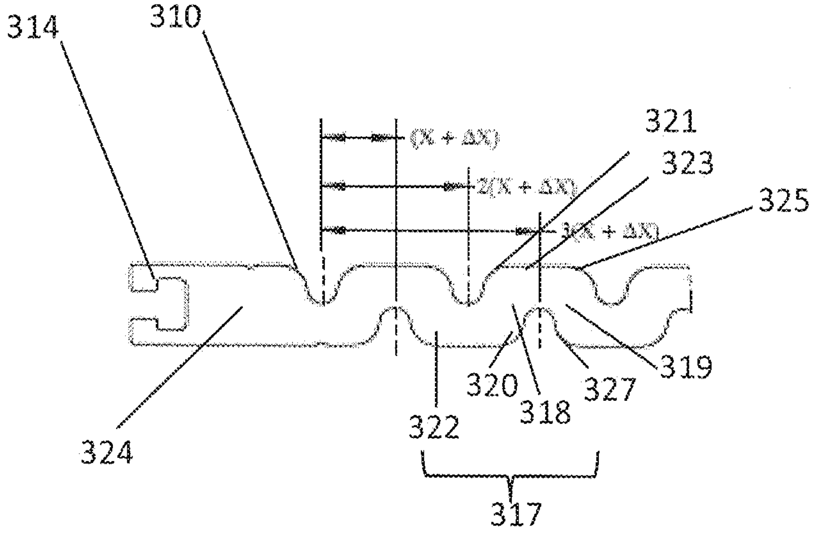
FIG. 11B is a side view of a portion of the actuator of FIG. 10 in the extended state.

With reference to FIG. 10, FIG. 11A, and FIG. 11B in some embodiments the extension element 316 can comprise a geometric profile defining a desired spring constant for the actuator 310. For example, in certain embodiments, the extension element 316 comprises a plurality of longitudinal sections 322 extending generally parallel to the central longitudinal axis, a plurality of transverse sections 318 extending transverse to the central longitudinal axis, and a plurality of bends 320 disposed between each longitudinal section of the plurality of longitudinal sections and an adjacent transverse section of the plurality of transverse sections. In certain embodiments, each bend 320 can comprise an arc segment having an inner radius and an outer radius. In certain embodiments, the extension element 316 can comprise a plurality of extension sections 317. In certain embodiments, each individual extension section 317 is a full section defined by a segment of a generally waveform-like profile extending from a peak to an adjacent peak (or a trough to an adjacent trough). Thus, each extension section 317 can comprise a first longitudinal segment 322, a first bend 320, a first transverse segment 318, a second bend 321, a second longitudinal segment 323, a third bend 325, a second transverse segment 319, and a fourth bend 327.

With continued reference to FIG. 10, FIG. 11A, and FIG. 11B, when a tensile force is applied to the actuator 310, a distance (X) (FIG. 11A) between adjacent longitudinal segments 322 will extend to an extended length (X+ΔX) (FIG. 11B) such that the overall length between the proximal end 312 and the distal end 314 is extended (FIG. 10). Thus, this extension characteristic of the actuator 310 can desirably limit a force applied by the jaw assembly of a surgical grasping instrument. In the event a user applies a relatively high force or attempts to grasp a relatively thick tissue sample, a portion of the applied force will extend the actuator, rather than being directly applied to grasped tissue.

With continued reference to FIG. 10, FIG. 11A, and FIG. 11B in certain embodiments, the dimensions of the longitudinal segments 322, bends 320, and transverse segments 318 can be sized and configured to provide an extension element 316 having a desired spring constant and resistance to fatigue. In certain embodiments, the actuator 310 is formed of a rigid material, such as a stainless-steel sheet material, which has elastic properties under controlled tensile loads. Desirably, the actuator 310 can have a substantially planar configuration with a width or thickness dimension being significantly smaller than a height or length dimension. In certain embodiments, whereas the surgical grasping instrument is introduced within 5 mm trocar delivery systems, the outer tube can have a maximum outer diameter of 0.197 inch and a minimum inner diameter of 0.140 inch. In certain embodiments, the actuator 310 positioned within the outer tube can have a height between 0.190 inch and 0.100 inch and have a thickness between 0.010 inch and 0.110 inch. Desirably, two actuators can have a combined thickness between 0.020 inch and 0.110 inch. In certain embodiments, multiple actuators can be assembled together in parallel, having a combined thickness between 0.020 inch and 0.110 inch. In certain embodiments, although the surgical grasping instrument is introduced within greater than 5 mm trocar delivery systems, the actuator 310 can have a maximum height of 0.350 inch and have a thickness between 0.010 inch and 0.250 inch. In some embodiments for use with an instrument sized and configured for placement through a 5 mm category access port such as a 5 mm trocar, the actuator 310 can have a thickness of approximately 0.040 inch. In certain embodiments, the actuator 310 can comprise a stack of two adjoining actuator members each having a thickness of approximately 0.020 inch.

With continued reference to FIG. 10, FIG. 11A, and FIG. 11B in certain embodiments, the extension element 316 can comprise at least 20 extension sections 317. Desirably, the extension element can comprise at least 30 extension sections 317. More desirably, in certain embodiments, the extension element 316 can comprise at least 40 extension sections 317. In certain embodiments, the extension element 316 can comprise 48 extension sections 317. While the illustrated embodiment includes a plurality of extension sections 317 that each have a consistent geometry, repeating to form the extension element 316, in other embodiments, the extension element 316 can be formed of various segment and bend geometries that have a variable pattern along a length of the actuator 310.

With continued reference to FIG. 10, FIG. 11A, and FIG. 11B, in certain embodiments the bends 320 can have an arc geometry defined by an inner radius and an outer radius. In other embodiments, the bends 320 can be formed by sections having sharp angles with no fillet or radii. In certain embodiments, the inner radius can be between about 0.02 inch and 0.08 inch. Desirably, a full radius defined by the inner radius can be between approximately 0.05 inch and 0.06 inch. In certain embodiments, the outer radius can be between approximately 0.024 inch and 0.054 inch. In some embodiments, the inner radius is greater than the outer radius. In other embodiments, the inner radius is less than the outer radius. In certain embodiments, a full radius defined by the inner radius is approximately 0.05 inch and the outer radius is approximately 0.044 inch. In other embodiments, a full radius defined by the inner radius is approximately 0.06 inch and the outer radius is approximately 0.036 inch.

In certain embodiments, the inner and outer radii can be sized and configured to provide an extension element 316 having a relatively constant width defined by a line tangent to an upper edge and a lower edge of the extension element 316. In certain embodiments, the width defined by the line tangent to the upper edge and the lower edge of the extension element 316 is between about 0.060 inch and 0.080 inch. Desirably, the width of the extension element 316 defined by the tangent line can be between about 0.065 inch and 0.075 inch. In certain embodiments, the width of the extension element 316 defined by the tangent line can be about 0.07 inches.

With continued reference to FIG. 10, FIG. 11A, and FIG. 11B, the extension element 316 of the actuator 310 can be spaced from the distal end 314 by a rigid element 324 defining a connector end with a straight section having a height greater than the width defined by the line tangent to the upper edge and the lower edge of the extension element 316. In some embodiments, the extension element 316 can be spaced apart from the distal end 314 by at least 0.2 inch. In other embodiments, the extension element 316 can be spaced from the distal end 314 by a connector end straight section having a minimal distance of as approximately 0.02 inch.

With continued reference to FIG. 10, FIG. 11A, and FIG. 11B, in certain embodiments, a total length of each full extension section 317 can be sized and configured to provide a desired spring constant and fatigue strength. In some embodiments, the length of each full extension section 317 can be between approximately 0.200 inch and 0.360 inch. Desirably, the length of each extension section 317 can be between approximately 0.240 inch and 0.260 inch. In certain embodiments, each extension section can have a length of approximately 0.240 inch. In other embodiments, each extension section can have a length of approximately 0.260 inch.

With continued reference to FIG. 10 and FIG. 11A, desirably, when a force applied to the actuator 310 by actuation of the movable handle is below a predetermined level, the actuator 310 translates within the outer tube 330 with the extension element 316 maintaining a constant length. Thus, with a relatively low force applied to the actuator 310, the actuator 310 functions as a solid rod actuator. The actuator 310 has a first length along the central longitudinal axis that remains constant on translation with application of a relatively low force to move the actuator 330 as a solid rod.

With reference to FIG. 10 and FIG. 11B, when a relatively high force is applied to the actuator 310, such as when a thick tissue specimen is inserted between the first and second jaws of the jaw assembly, the extension element 316 can stretch in response, thereby reducing the effective stroke length of the actuator 310 at the distal end 314. In some embodiments, the actuator 310 functions as a spring-like actuator. Thus, upon application of a predetermined extension force, the actuator 310 extends to a second length greater than the first length. In this higher force loading condition, the actuator 310 both translates within the outer tube 330 and extends in length between the proximal end 312 and the distal end 314. This reduced effective stroke length provided by extension of the extension element 316 advantageously limits the force applied by the end effector or jaw assembly and correspondingly reduces a risk of trauma to tissue grasped by the jaw assembly. The actuator 310 provides this force limiting performance as a single, integral component without the added mechanical and manufacturing complexities and increased expenditures of one or more additional springs. Desirably, the extension element 316 of the actuator 310 is sized and configured to deform elastically when a relatively high force is applied thereto as illustrated in FIG. 11B such that once the force is released, the actuator 310 returns to its original, undeformed state and length.

In a further embodiment, the actuator 310 is also sized and configured to supplement the first and second jaws of the jaw assembly with force that was loaded into the actuator 310 (which caused the actuator 310 to deform elastically as described above). In some cases, the jaw assembly may be locked in a closed position with tissue that is being grasped between the first and second jaw. The extent that the jaw assembly is in contact with the tissue is based on the thickness and/or volume of the tissue being grasped as well as the pre-determined amount of force that is provided to the tissue. However, if the tissue deforms (e.g., as fluids leave or are pushed out of the cells associated with the grasped tissue) which causes the thickness and volume of tissue being initially grasped to decrease, the original contact between the tissue and the jaw assembly may no longer be possible. Furthermore, in a conventional surgical grasper with a rigid, non-elastic actuator, since the first and second jaws of the jaw assembly are locked, tissue deformation may prevent the jaw assembly from properly grasping the tissue possibly causing the contact with the tissue to become loose or even slip from the jaw assembly.

Desirably, certain embodiments of the surgical grasping device described herein can provide a dynamic amount of force from the actuator 310 in order to maintain constant and/or consistent contact with the tissue between the first and second jaws of the jaw assembly as the tissue deforms. The dynamic amount of force being provided to the jaw assembly is supplied from the excess force that was previously loaded into the actuator 310. As discussed above, the actuator 310 may extend from a first length to a second greater length when loading force being provided by the user (via the movable handle). As the thickness and volume of tissue that was initially grasped between the first and second jaws of the jaw assembly changes (e.g., via deformation), a response from the actuator 310 can provide the force that was loaded into the actuator 310 to the jaw assembly so that the first and second jaws are pivoted closer towards each other in order to maintain contact with the tissue. This force, as it leaves the actuator 310, causes the actuator 310 to retract from the second greater length back towards the first length. The response from the actuator 310 provides additional force to the first and second jaws as needed to maintain contact with the deforming/deformed tissue based on the extent the thickness and volume of the tissue changes over time. In this way, contact with the tissue, as the tissue deforms, can be made constant/consistent between the first and second jaws of the jaw assembly.

Figure 12:
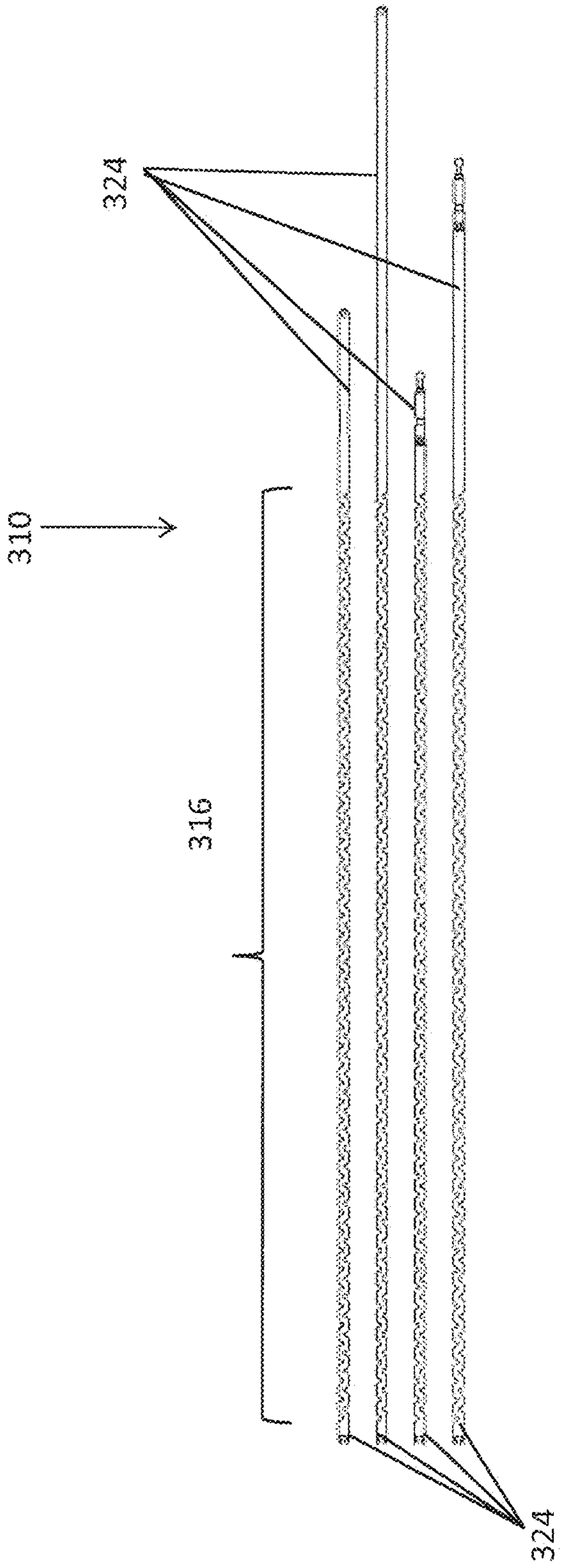
FIG. 12 is a side view of various embodiments of actuator having an extension element.

With reference to FIG. 10 and FIG. 12, various embodiments of the actuator 310 are illustrated having different lengths of rigid element 324 adjacent the proximal end. As illustrated, the extension element 316 of the actuator 310 can be spaced from the proximal end 312 by a rigid element 324 having a height greater than a width of the extension element 316 defined by a line tangent to the upper edge and the lower edge of the extension element 316. In certain embodiments, it can be desired that the length of rigid element 324 adjacent the proximal end be relatively long to conform to surgical instruments having different dimensions or operational configurations. For example, as illustrated in FIG. 12, an extension element 316 having a substantially similar configuration can be used in each of a 35 cm length single-use grasper (uppermost illustrated actuator), a 45 cm single-use grasper (second actuator from top), a 38 cm reposable grasper shaft (third actuator from top), and a 45 cm reposable grasper shaft (lowermost actuator). Alternatively, by varying the length of the extension element 316 relative to the lengths of the rigid elements 324 at the proximal and distal ends 213, 314 of the actuator 310, desired extension properties of the actuator 310 can be achieved.

With reference to FIG. 10-FIG. 12, the illustrated embodiments include a planar actuator 310 with an extension element 316 integrally formed therewith. Advantageously, this planar actuator can provide manufacturing efficiencies and can fit within and be constrained for translation within a relatively small space, such as an elongate shaft assembly sized for insertion through a surgical access port for 5 mm laparoscopic instruments. In other embodiments, it is contemplated that other actuator configurations can provide a desired integrated force-limiting extension element.

Figure 13:
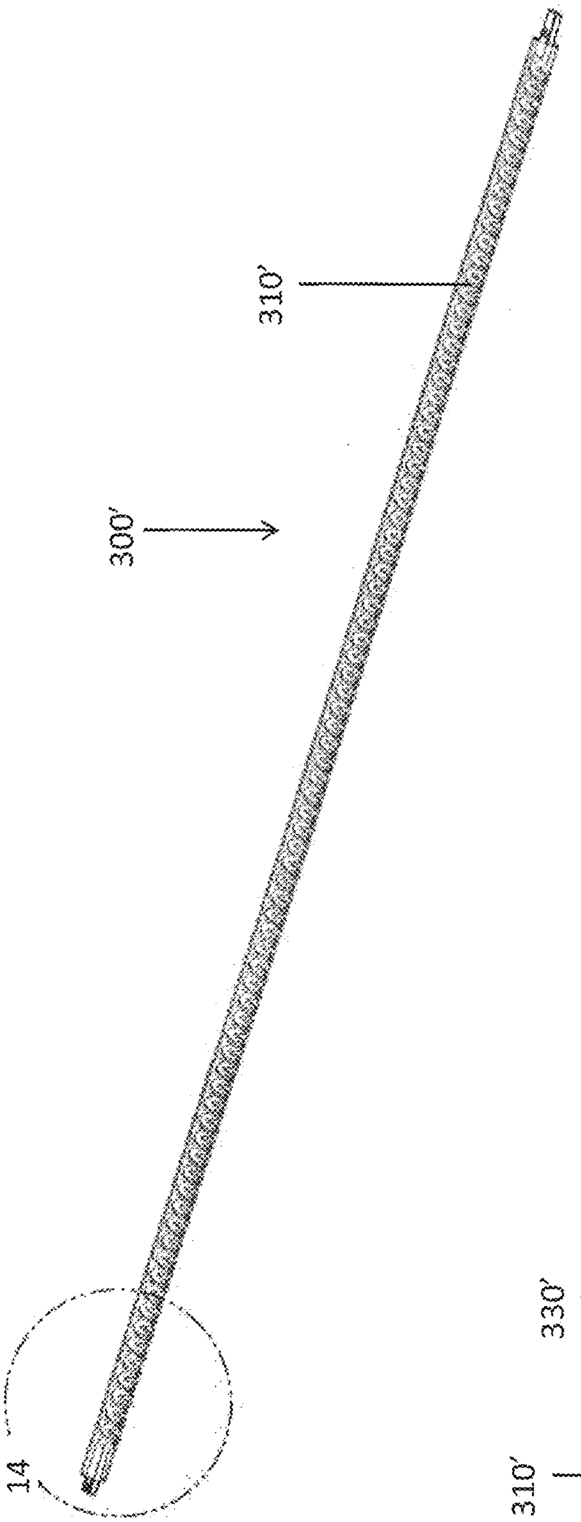
FIG. 13 is a partial cut away side view of a shaft assembly of an embodiment of surgical instrument with an embodiment of actuator with an extension element.
Figure 14:
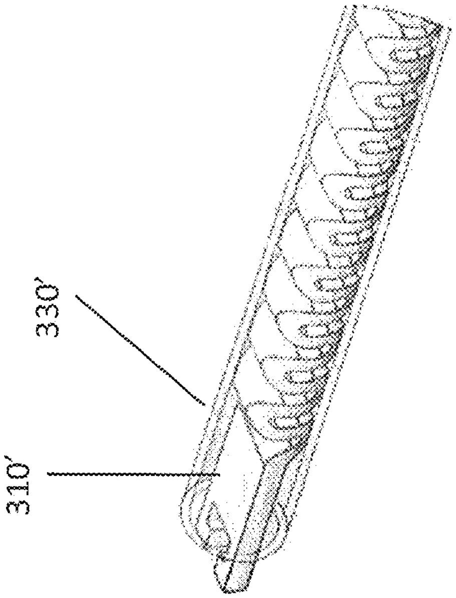
FIG. 14 is a partial cut away side view of a section of the shaft assembly of FIG. 13.

With reference to FIG. 13 and FIG. 14, a partial cut-away side view of an embodiment of elongate shaft assembly 300' for use in a surgical instrument is illustrated. In the illustrated embodiment, the elongate shaft assembly 300' comprises an actuator 310' having a non-planar configuration with a generally repeating waveform or convoluted profile. This convoluted profile can desirably allow the actuator 310' to extend when a relatively high force is applied while still performing as a solid rod actuator, as discussed above with respect to actuator 300. In some embodiments, the non-planar actuator 310' configuration can provide flexibility such that the actuator 310' can be disposed within a flexible outer tube 330' or an outer tube having a curvature, rather than constrained within a relatively rigid outer tube. In some embodiments, the actuator 310' can comprise a metallic material, in other embodiments, the actuator 310' can comprise a polymeric material, and in other embodiments, the actuator 310' can comprise a polymer-metal composite material. In certain embodiments, a convoluted, non-planar actuator 310' can be formed of a polymeric material through an injection molding process. In other embodiments, a convoluted, non-planar actuator 310' can be formed of a polymeric material through an extrusion process.

With continued reference to FIG. 13 and FIG. 14, the convoluted profile of the actuator 310' defining a relieved cylindrical outer surface. This convoluted profile can desirably a provide enhanced flexibility about two orthogonal axes such that the actuator 310' can be disposed within a flexible outer tube 330' or an outer tube having a curvature, rather than constrained within a relatively rigid outer tube.

Figure 15:
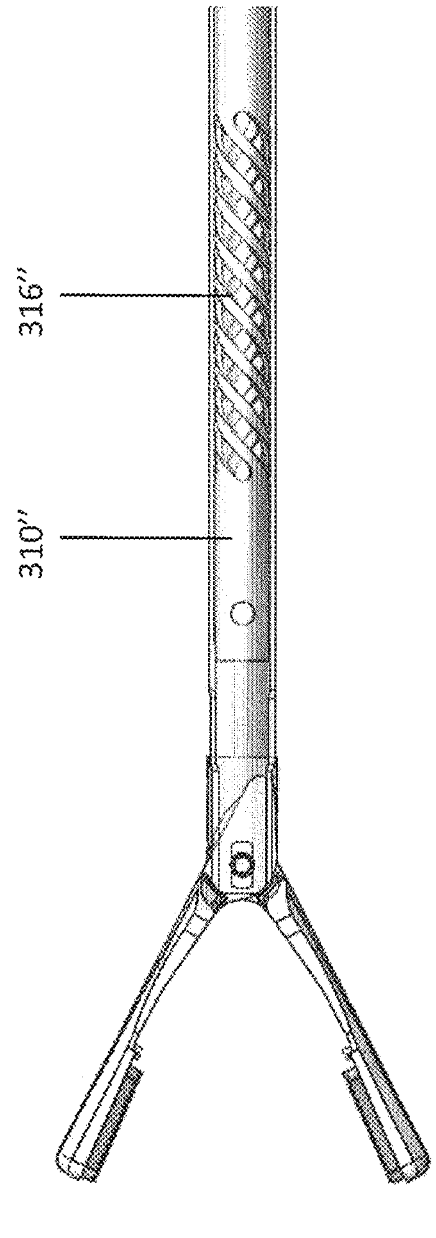
FIG. 15 is a partial cut away side view of a shaft assembly of an embodiment of surgical instrument with an embodiment of actuator with an extension element.

With reference to FIG. 15, in some embodiments, an actuator 310" can comprise a hollow tubular member with relief slots 316" formed therein to define a flexible and extendable segment therein. These relief slots can desirably allow the slotted-tube actuator to extend when a relatively high force is applied while still performing as a solid rod actuator, as discussed above with respect to actuator 300. In some embodiments, as with the non-planar actuators 310' the slotted-tube actuator 310" can provide flexibility about multiple orthogonal axes such that the slotted-tube actuator can be disposed within a flexible outer tube or an outer tube having a curvature, rather than constrained within a relatively rigid outer tube. In some embodiments, the slotted-tube actuator can comprise a metallic material, in other embodiments, the slotted-tube actuator can comprise a polymeric material, and in other embodiments, the slotted-tube actuator can comprise a polymer-metal composite material.

It is contemplated that various other actuator configurations can provide similar integrated extension element performance as described herein with respect to a planar sheet actuator. For example, in certain other embodiments, surgical instruments can include an actuator comprised of or formed from a wire, such as for example a wire having a solid, round, semi-circular, rectangular, or square cross-sectional profile, or braided rope cables formed of multiple wire or filament strands. Additionally, it is contemplated that while certain embodiments of planar actuator are described as formed of a metallic material, in other embodiments, the actuator can be formed of a polymeric material. Furthermore, while the actuation mechanisms are discussed herein with respect to certain advantages in a surgical grasper instrument, it is contemplated that various aspects of the actuation mechanisms can likewise provide advantages in other surgical instruments and in various devices outside the medical field in which it can be desirable to provide an extension element that operates as a solid rod actuator with a relatively low applied force and an extension element with a relatively high applied force.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above but should be determined only by a fair reading of the claims granted on a related non-provisional application.

What is claimed is:

1. A surgical instrument comprising:

a handle assembly comprising:

a stationary handle, a movable handle pivotably coupled to the stationary handle, and a locking mechanism comprising:

a locking member having a lock portion extending within the handle assembly and a trigger portion extending adjacent an outer surface of the stationary handle, the locking member movable between a locked position in which the trigger portion is separated from the stationary handle and an unlocked position in which the trigger portion is approximated with the stationary handle, and a lock release coupled to the stationary handle, wherein the lock release maintains the locking member in the unlocked position, and wherein the trigger portion is maintained in the unlocked position adjacent the stationary handle by latching engagement with the lock release, and wherein the lock release is actuatable out of engagement with the trigger portion to allow the locking member to move from the unlocked position to the locked position;

an elongate shaft extending distally from the handle assembly, the elongate shaft having a proximal end coupled to the handle assembly, a distal end opposite the proximal end, and a central longitudinal axis defined by the proximal end and the distal end, the elongate shaft comprising:

an outer tube, and an actuator positioned longitudinally within the outer tube, the actuator having a sliding fit with the outer tube, and the actuator being responsive to pivotal movement of the movable handle, the actuator having a proximal section extending within the handle assembly to a proximal end and the actuator comprising a locking surface adjacent the proximal end; and an end effector at the distal end of the elongate shaft, the end effector movable between a first configuration and a second configuration responsive to pivotal movement of the movable handle, wherein the lock portion of the locking member is engaged with the locking surface of the actuator with the locking mechanism in the locked position thereby restricting the actuator from freely translating proximally and distally within the elongate shaft.

2. The surgical instrument of claim 1, wherein the locking mechanism further comprises a locking spring within the handle assembly, the locking spring configured to bias the lock portion of the locking member to maintain an engagement with the actuator when in the locked position.

3. The surgical instrument of claim 1, wherein the locking surface of the actuator is a recess formed within the actuator and sized to selectively engage with the lock portion of the locking mechanism.

4. The surgical instrument of claim 1, wherein the lock portion comprises a passage formed therein and configured to allow the actuator to freely translate while the locking member is in the unlocked position.

5. The surgical instrument of claim 4, wherein the passage is misaligned with respect to an axis perpendicular to a longitudinal axis of the actuator while the locking member is in the locked position thereby engaging with the actuator.

6. The surgical instrument of claim 1 wherein the end effector comprises a jaw assembly configured to grasp tissue, the jaw assembly having an open position corresponding to the first configuration and a closed position corresponding to the second configuration, and wherein the locking mechanism is configured to define a reverse limit that restricts an extent the jaw assembly reverts from the closed position back to the open position.

7. The surgical instrument of claim 1, wherein the locking mechanism further comprises a pivot pin, and wherein the movable handle is pivoted relative to the stationary handle about the pivot pin.

8. The surgical instrument of claim 7, wherein the pivot pin is located between a first end of the movable handle and a second end of the movable handle, and wherein the second end of the movable handle is coupled to the proximal end of the actuator.

9. The surgical instrument of claim 8, wherein the proximal end of the actuator comprises a proximal coupler configured to couple the actuator to second end of the movable handle.

10. The surgical instrument of claim 9, wherein the proximal coupler comprises at least one of a recess, bore, or slot in the actuator.

11. The surgical instrument of claim 1, wherein the locking mechanism is further configured to maintain the movable handle in a set position while in the locked position.

12. The surgical instrument of claim 1, wherein the lock release is pivotally coupled to the stationary handle at a lock release pivot point, and wherein interacting with the lock release allows the locking member to transition from the locked position into the unlocked position.

13. The surgical instrument of claim 12, wherein the lock release is biased using a lock release spring, and wherein the interaction includes depressing the lock release to overcome the bias of the lock release spring.

14. The surgical instrument of claim 1, wherein the actuator is configured to have a first length along the central longitudinal axis of the elongate shaft, the actuator comprises a plurality of planar extension elements that lengthens the actuator to a second length greater than the first length along the central longitudinal axis in response to a predetermined force applied to the actuator via the movable handle, and wherein the lengthening of the actuator is configured to limit an amount of force received from the movable handle above a pre-determined threshold that is provided to the end effector.

15. A surgical instrument comprising:

a handle assembly comprising a stationary handle and a movable handle, wherein the movable handle is pivotably coupled to the stationary handle;

an elongate shaft extending distally from the handle assembly, the elongate shaft having a proximal end coupled to the handle assembly, a distal end opposite to the proximal end and coupled to a jaw assembly having an open and closed configuration, and a central longitudinal axis defined by the proximal end and the distal end of the elongate shaft, the elongate shaft comprising:

an outer tube, and an actuator positioned longitudinally within the outer tube, the actuator being responsive to pivotal movements of the movable handle and configured to open and close the jaw assembly in response to movements of the movable handle; and a locking mechanism comprising:

a locking member movable between a locked position in which a trigger portion of the locking member is separated from the stationary handle and an unlocked position in which the trigger portion of the locking member is approximated with the stationary handle, the locking member configured to engage with the actuator to restrict movement of the actuator within the elongate shaft and maintain a position of the movable handle, and a lock release maintaining the locking member in the unlocked position by latching engagement with the lock release, the lock release actuatable out of engagement with the locking member to allow the locking member to move from the unlocked position to the locked position, wherein the lock release is coupled to the stationary handle.

16. The surgical instrument of claim 15, wherein the locking mechanism further comprises a locking spring within the handle assembly, the locking spring configured to bias the locking mechanism to maintain an engagement with the actuator when in the locked position.

17. The surgical instrument of claim 15, wherein the actuator comprises a locking surface that is configured to selectively engage with the locking mechanism to restrict movement of the actuator while the locking mechanism is in the locked position.

18. The surgical instrument of claim 15, wherein the locking member comprises a lock portion having a passage formed therein that allows the actuator to pass therethrough and freely translate while the locking member is in the unlocked position, and wherein the passage is configured to engage with the actuator when the locking member is in the locked position thereby preventing the actuator from freely translating, wherein the passage is arranged such that the passage is misaligned with respect to an axis perpendicular to a longitudinal axis of the actuator.

19. The surgical instrument of claim 15, wherein the locking mechanism further defines a reverse limit that restricts an extent the jaw assembly is able to revert from the closed configuration to the open configuration.

20. The surgical instrument of claim 15, wherein the actuator is configured to have a first length along the central longitudinal axis of the elongate shaft, the actuator comprises a plurality of planar extension elements that lengthens the actuator to a second length greater than the first length along the central longitudinal axis in response to a predetermined force applied to the actuator via the movable handle, and wherein the lengthening of the actuator is configured to limit an amount of force received from the movable handle above a pre-determined threshold that is provided to the jaw assembly.

* * * * *